(12) United States Patent  
Denham et al.

(10) Patent No.: US 11,660,202 B2  
(45) Date of Patent: May 30, 2023

(54) JOINT ARTHROPLASTY DEVICE AND METHOD

(71) Applicant: NEXTREMITY SOLUTIONS, INC., Warsaw, IN (US)

(72) Inventors: Greg Denham, Warsaw, IN (US); Ryan Schlotterback, Warsaw, IN (US); John Pepper, Warsaw, IN (US)

(73) Assignee: MEDARTIS AG, Basel (CH)

( * ) Notice: Subject to any disclaimer, the term of this patent is extended or adjusted under 35 U.S.C. 154(b) by 0 days.

(21) Appl. No.: 16/593,578

(22) Filed: Oct. 4, 2019

(65) Prior Publication Data

US 2020/0107937 A1 Apr. 9, 2020

Related U.S. Application Data

(60) Provisional application No. 62/741,223, filed on Oct. 4, 2018.

(51) Int. Cl.
| | | |
|---|---|---|
| *A61F 2/42* | (2006.01) | |
| *A61F 2/46* | (2006.01) | |
| *A61F 2/30* | (2006.01) | |

(52) U.S. Cl.
CPC .......... *A61F 2/4225* (2013.01); *A61F 2/4606* (2013.01); *A61F 2002/302* (2013.01);
(Continued)

(58) Field of Classification Search
CPC .. A61F 2/4225; A61F 2/30; A61F 2/42; A61F 2/4202; A61F 2/3099; A61F 2/4405; A61F 2/44; A61F 2/38; A61F 2/3804; A61F 2/3859; A61F 2/389; A61F 2/32; A61F 2/40; A61F 2/3877; A61F 2/36; A61F 2002/4233; A61F 2002/4256; A61F 2002/4271; A61F 2002/4228; A61F 2002/4238; A61F 2002/4243; A61F 2002/4251; A61F 2002/30995; A61F 2002/2828; A61F 2002/30731;
(Continued)

(56) References Cited

U.S. PATENT DOCUMENTS 5,263,987 A 11/1993 Shah  
7,585,327 B2 * 9/2009 Winslow ............... A61F 2/4003  
623/23.42

(Continued)

FOREIGN PATENT DOCUMENTS

EP 1708653 B1 9/2009  
FR 3022137 A1 12/2015

OTHER PUBLICATIONS

International Search Report and Written Opinion for International Patent Application No. PCT/US19/54817 dated Dec. 23, 2019.

*Primary Examiner* — Brian A Dukert  
(74) *Attorney, Agent, or Firm* — Heslin Rothenberg Farley & Mesiti P.C.; Victor A. Cardona, Esq.

(57) ABSTRACT

An implant having a joint facing surface and a bone facing surface forming a body member and a dorsal member therebetween. The implant further having a ring member extending out from the bone facing surface to a free end disposed for insertion into a bone recess. The body member and the dorsal member include a concave curvature on the bone facing surface and a convex curvature on the joint facing surface.

16 Claims, 25 Drawing Sheets

(52) U.S. Cl.
CPC .............. *A61F 2002/30822* (2013.01); *A61F 2002/4233* (2013.01)

(58) Field of Classification Search
CPC ...... A61F 2002/30822; A61F 2002/302; A61F 2220/0016; A61F 2/3601; A61F 2/3603; A61F 2/4014; A61F 2/4081
See application file for complete search history.

(56) References Cited

U.S. PATENT DOCUMENTS

| | | | |
|---|---|---|---|
| 7,618,462 B2 | 11/2009 | Ek | |
| 8,157,870 B2 * | 4/2012 | Kropf | A61F 2/4003 623/23.12 |
| 8,591,581 B2 | 11/2013 | Strzepa et al. | |
| 8,690,956 B2 | 4/2014 | Cook et al. | |
| 9,931,219 B2 * | 4/2018 | Sikora | A61F 2/4637 |
| 10,617,528 B2 * | 4/2020 | Lauf | A61F 2/4225 |
| 10,624,748 B2 * | 4/2020 | Ek | A61F 2/4003 |
| 2006/0074492 A1 | 4/2006 | Frey | |
| 2008/0255671 A1 * | 10/2008 | Kriek | A61F 2/384 623/20.14 |
| 2010/0312342 A1 | 12/2010 | Ek | |
| 2011/0093085 A1 * | 4/2011 | Morton | A61B 17/15 623/21.19 |
| 2011/0184528 A1 | 7/2011 | Beckendorf et al. | |
| 2012/0179268 A1 | 7/2012 | Hollawell | |
| 2014/0207241 A1 | 7/2014 | Lilly et al. | |
| 2015/0250594 A1 | 9/2015 | Ek | |
| 2017/0100251 A1 | 4/2017 | Ek et al. | |
| 2017/0224499 A1 | 8/2017 | Clarke et al. | |

\* cited by examiner

JOINT ARTHROPLASTY DEVICE AND METHOD

CROSS-REFERENCE TO RELATED APPLICATIONS

This application claims priority under 35 U.S.C. § 119 to U.S. Provisional Application No. 62/741,223, filed Oct. 4, 2018, which is herein incorporated by reference in its entirety.

BACKGROUND OF THE INVENTION

Technical Field

The present invention generally relates to joint arthroplasty. More particularly, the present invention relates to hemiarthroplasty.

Background Information

The metatarsal phalangeal joint (MPJ) of the hallux is high loaded and can experience over 100 percent of body weight through its surface.

Arthritis limits joint motion and alters joint mechanics, resulting in cartilage erosion and bone on bone contact. A damaged or arthritic joint causes considerable pain and loss of mobility. Yet, patients are reluctant to fuse a joint. Current treatment is by fusion which stops pain, but limits mobility.

Alternative treatments using hydrogels placed in a joint, provide pain relief but are generally not strong enough to correct joint motion issues. Hydrogels also have a record of subsidence and joint collapse. Silicone joints are another alternative but do not perform well long term.

Thus, a need exists for an alternative to joint fusion that corrects joint motion issues and provides pain relief.

SUMMARY OF THE INVENTION

In one aspect of the invention, an implant is provided, having a joint facing surface and a bone facing surface forming a body member and a dorsal member therebetween. The implant further having a ring member extending out from the bone facing surface to a free end disposed for insertion into a bone recess. The body member and the dorsal member include a concave curvature on the bone facing surface and a convex curvature on the joint facing surface.

In another aspect of the invention, an implant is provided, having a joint facing surface and a bone facing surface forming a body member therebetween. The implant further having a ring member extending out from the bone facing surface to a free end disposed for insertion into a bone recess and a dorsal member extending from a dorsal end of the body member.

In another aspect of the invention, a bone preservation method is provided, including removing joint cartilage, preparing a bone head region of a metatarsal bone, removing a ring-shaped segment of a cortical bone layer, and forming a ring-shaped recess. The method further including, applying an implant to the bone head region, with the implant having a joint facing surface and a bone facing surface, forming a body and a dorsal member therebetween, and ring member extending from the bone facing surface. The method further including inserting the ring member into the ring-shaped recess, and affixing the dorsal member of the implant to a dorsal region of the metatarsal bone, with the implant extending from the bone head to the dorsal region.

These, and other objects, features and advantages of this invention will become apparent from the following detailed description of the various aspects of the invention taken in conjunction with the accompanying drawings.

DETAILED DESCRIPTION OF THE INVENTION

Figure 1:
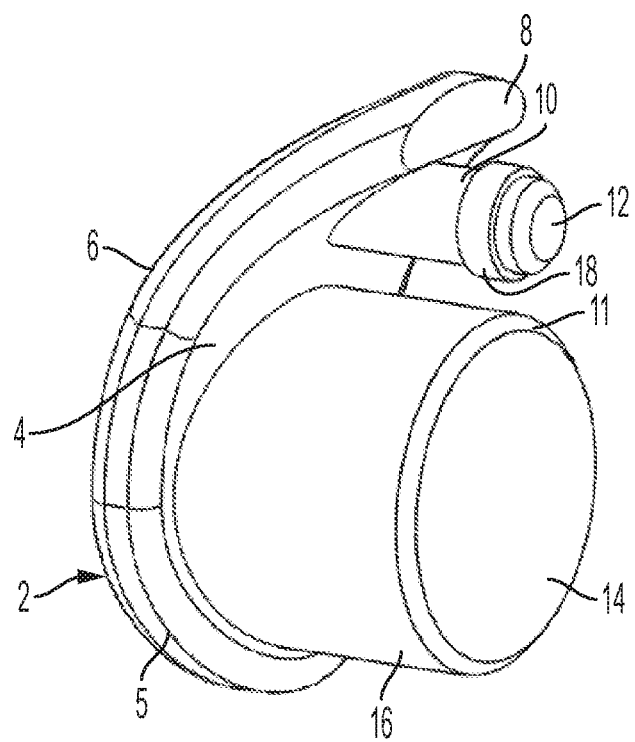
FIG. 1 is a perspective view of a dual post hemiarthroplasty device, in accordance with an aspect of the present invention.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for use in femoral cerclage fixation. However, those possessing an ordinary level of skill in the relevant art will appreciate that fixation of other bones are suitable for use with the foregoing systems, methods, and apparatuses. Likewise, the various figures, steps, procedures, and work-flows are presented only as an example and in no way limit the systems, methods or apparatuses described to performing their respective tasks or outcomes in different time-frames or orders. The teachings of the present invention may be applied to cerclage related to any bone.

Furthermore, there is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts. Hence, specific dimensions and other physical characteristics relating to the embodiments disclosed herein are not to be considered as limiting, unless expressly stated otherwise.

The various embodiments described herein provide for systems, apparatuses, devices, and methods for joint arthroplasty and hemiarthroplasty. The various figures and description may refer to first metatarsal phalangeal joint. However one having ordinary skill in the art will understand that that the following systems, apparatuses, devices, and methods for joint arthroplasty may be used with other joints, such as the temporomandibular joint, spinal facet joints, spinal discs, the carpometacarpal, the distal interphalangeal, the sacroiliac, the ankle, carpal bone joints, the elbow, the knee, the hip, the shoulder, small joints in the foot and the hand, the fore foot, the patella, and reconstruction of the labrum.

Figure 40:
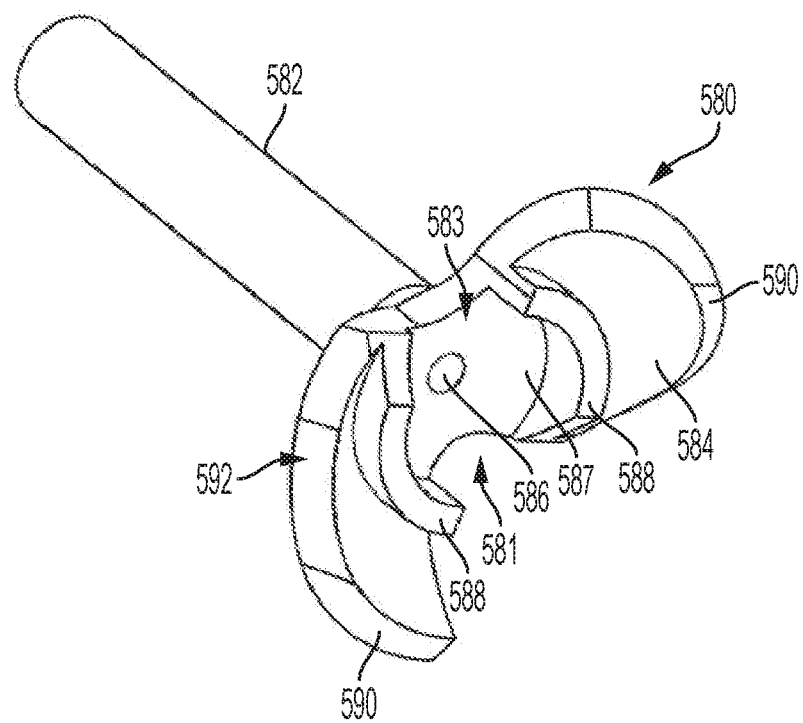
FIG. 40 is a perspective view of a cannulated cup shaped reamer, in accordance with an aspect of the present invention.
Figure 41:
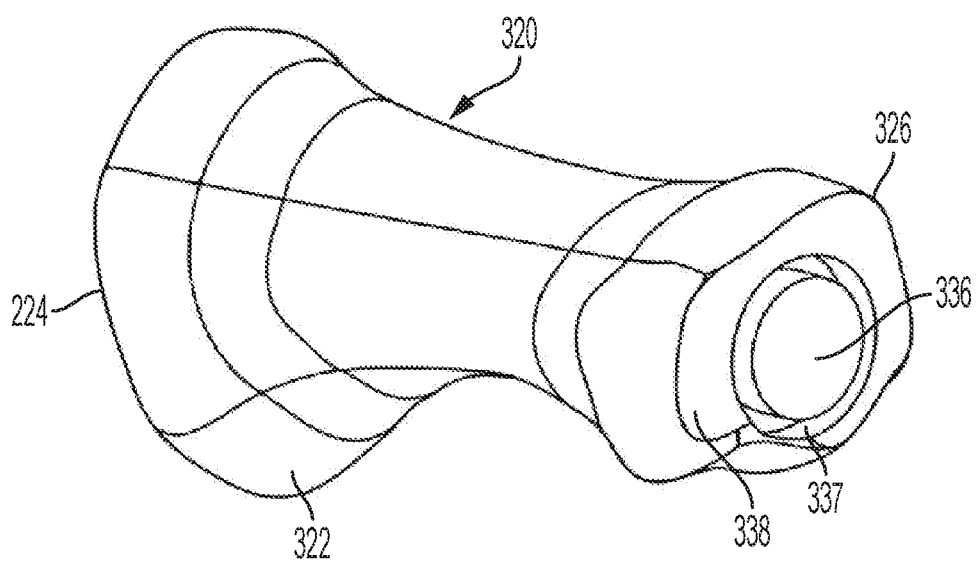
FIG. 41 is a perspective view of the metatarsal bone of FIG. 18 prepared using a cup shaped reamer, in accordance with an aspect of the present invention.

Referring to the drawings, wherein like reference numerals are used to indicate like or analogous components throughout the several views, and with particular reference to FIGS. 1-39 and 42-51 a hemiarthroplasty device, is depicted in various embodiments. Hemiarthroplasty device may also be referred to as an implant. With reference to FIGS. 18, 19, 25-32, 38, and 39, a metatarsal bone 320 is depicted with various embodiments of hemiarthroplasty device. With reference to FIG. 20 a phalangeal bone 340 is depicted with an embodiment of hemiarthroplasty device engaged therein. With reference to FIGS. 40 and 41, a reamer and metatarsal bone 320 with a reface for engagement with hemiarthroplasty device.

With reference to FIG. 1 a first embodiment is depicted as a dual post hemiarthroplasty device or an implant 2 having an exterior surface or joint facing surface 6 and a bone facing surface 4 forming a body 5 therebetween. Joint facing surface 6 and bone facing surface 4 are depicted extending dorsally from body 5 forming a dorsal hood 8 therebetween. Body 5 and dorsal hood 8 may, for example, form an ovular button shape. Dorsal hood 8 may also, for example, curve towards bone facing surface 4. A primary post 16, having a cylindrical shape, is depicted extending away from bone facing surface 4 towards a tapered region 11 and a free end 14. A secondary post 10 extends from bone facing surface 4 of dorsal hood 8 towards a free end 12. Secondary post 10 may also, for example have, a barbed region 18 between bone facing surface 4 and free end 12. Implant 2 is configured (e.g. shaped and dimensioned) for attachment to a bone surface, with primary post 16 configured (e.g. shaped and dimensioned) for insertion into a prepared hole in a bone end and with secondary post 10 configured (e.g. shaped and dimensioned) for insertion in a dorsal region of the bone end. Barbed region 18 may, for example, promote bone fixation.

Figure 2:
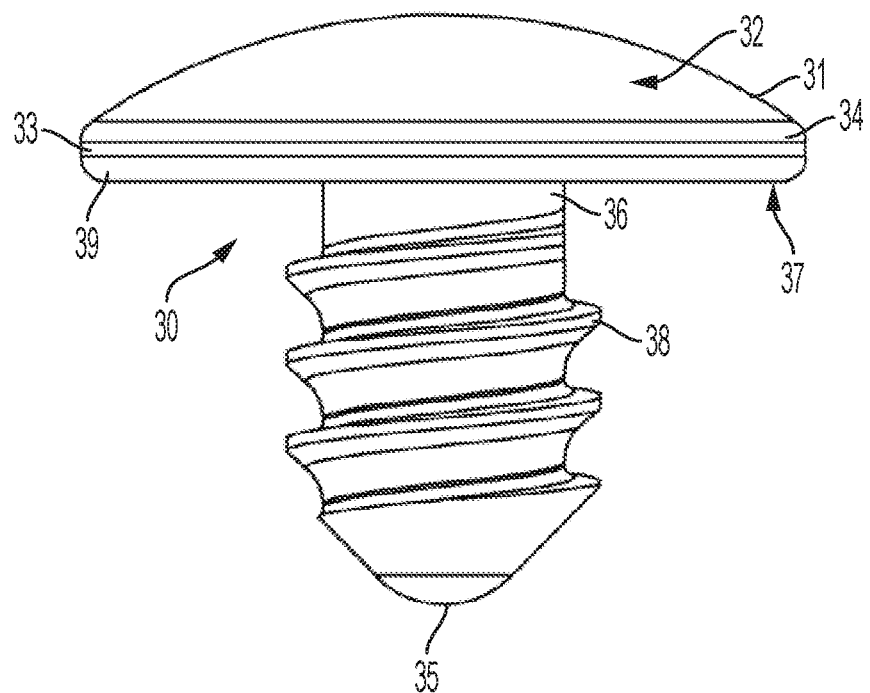
FIG. 2 is a perspective view of threaded post hemiarthroplasty device, in accordance with an aspect of the present invention.

Referring to FIG. 2, another embodiment is depicted as a single post hemiarthroplasty device or an implant 30 having a post 36 extending from a cap 32. Post 36 may have, for example threading 38 extending towards a free end 35. Cap 32 may have, for example, a domed region or exterior region 31. Cap 32 is further depicted having tapered region 34 between domed region 31 and a ringed region 33 around a base ring 39 of domed region 31. Cap 32 may further have a bone facing surface 37 from which post 36 extends. Bone facing surface 37 may, for example, be a planar surface extending from base ring 39 in towards post 36 or bone facing surface 37 may be concave extending from base ring 39 towards post 36.

Figure 3:
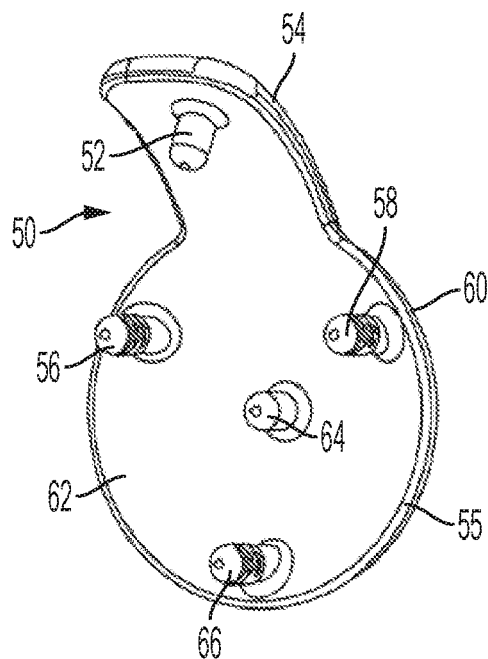
FIG. 3 is a first perspective view of a multiple post hemiarthroplasty device, in accordance with an aspect of the present invention.
Figure 4:
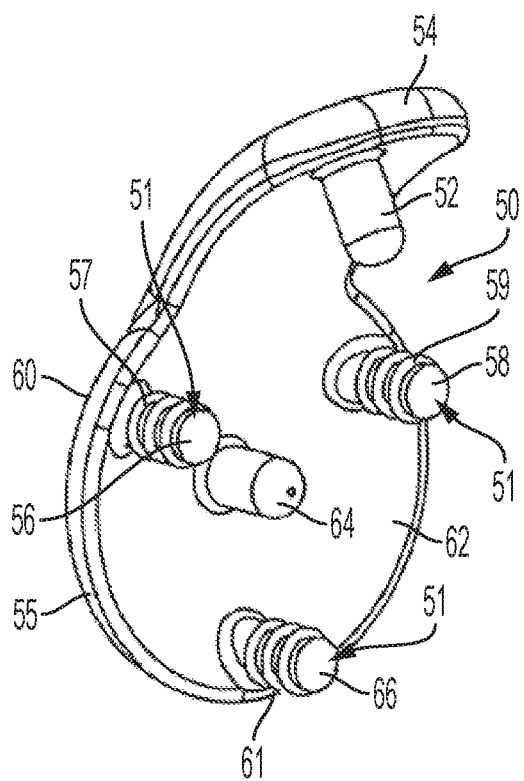
FIG. 4 is a second perspective view of the multiple post hemiarthroplasty device of FIG. 3, in accordance with an aspect of the present invention.

Referring to FIGS. 3-4, a further embodiment is depicted as a multi-post hemiarthroplasty device or an implant 50 having an exterior surface or joint facing surface 60 and a bone facing surface 62 forming a body 55 therebetween. Body 55 may be, for example, button-shaped. Joint facing surface 60 and bone facing surface 62 are depicted extending dorsally from body 55 forming dorsal hood 54 therebetween. Dorsal hood 54 may, for example, be an elongated extension or appendage from body 55. Dorsal hood 54 may also, for example, curve towards bone facing surface 62. A central post 64 is depicted, extending out form approximately the center of bone facing surface 62, away from joint facing surface 60, having a cylindrical shape. A plurality of posts 51 having a cylindrical shape are depicted as having barbed surfaces and extending out from bone facing surface 62, away from joint facing surface 60, and positioned towards the perimeter of body 55. A first post 56 having a barbed surface 57, a second post 58 having a barbed surface 59, and a third post 66 having a barbed surface 61 are depicted. A dorsal post 52 is depicted as having a cylindrical shape and extending out from bone facing surface 62, away from joint facing surface 60, of dorsal hood 54. Central post 64, plurality of posts 51, and dorsal post 52 are depicted as having domed shaped free ends. Barbed surfaces (e.g. 57, 58, 59) may, for example, promote bone fixation.

Figure 5:
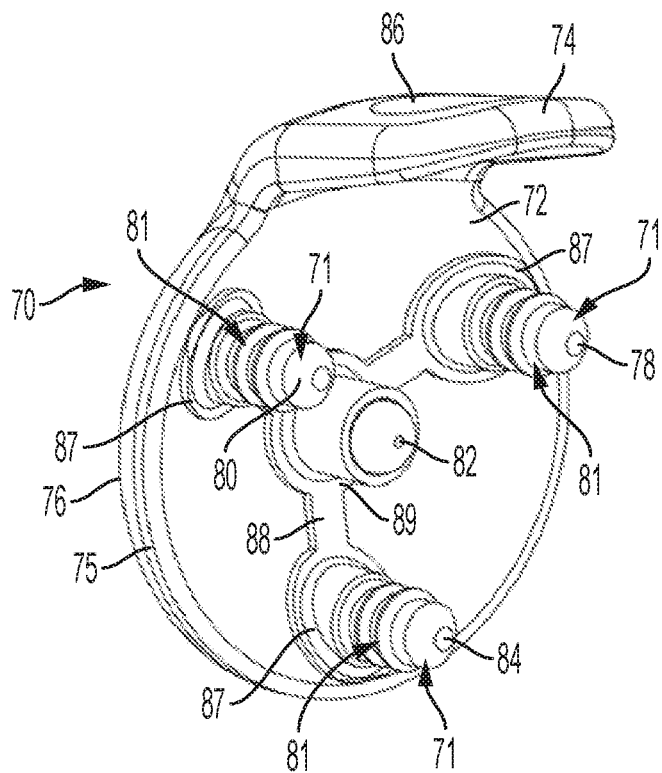
FIG. 5 is a perspective view of a multiple post hemiarthroplasty device with a metallic stiffening structure, in accordance with an aspect of the present invention.

Referring to FIG. 5, yet another embodiment is depicted as a multi-post hemiarthroplasty device or an implant 70 having an exterior surface or joint facing surface 76 and a bone facing surface 72 forming a body 75 therebetween. Joint facing surface 76 and bone facing surface 72 are depicted extending dorsally from body 75 forming dorsal hood 74 therebetween. Dorsal hood 74 may, for example, be an elongated extension or appendage from body 55. Dorsal hood 74 is depicted as extending at an angle from bone facing surface 72 of body 55, and away from joint facing surface 76. A central post 82 is depicted, extending out form approximately the center of bone facing surface 72, away from joint facing surface 76, having a cylindrical shape. A plurality of posts 71 are depicted extending out from bone facing surface 72, away from joint facing surface 76, and positioned towards the perimeter of body 75. Plurality of posts 71 are further depicted as having a cylindrical shape and with barbed surfaces 81. Plurality of posts 71 may include, for example, a first post 78, a second post 84, and a third post 82. A dorsal screw retention hole 86 may, for example, extend from joint facing surface 76 to bone facing surface 72 of dorsal hood 54. Central post 82 and plurality of posts 71 are depicted as having domed shaped free ends. Central post 82 and plurality of posts 71 may also be connected by a reinforcing structure 88. Reinforcing structure 88 may have, for example, a plurality of encircling components 87 around plurality of posts 71 with connecting members extending to a central encircling component 89 around central post 82. Barbed surfaces 82, may, for example, aid in promoting bone fixation.

Figure 6:
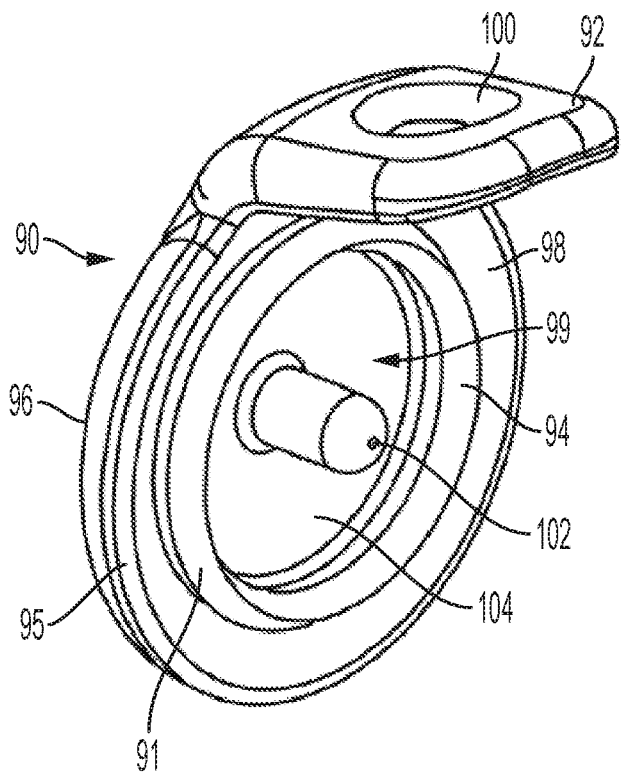
FIG. 6 is a perspective view of retainer ring hemiarthroplasty device with a central post, in accordance with an aspect of the present invention.

Referring to FIG. 6, another embodiment is depicted as a multi-post hemiarthroplasty device or an implant 90 having an exterior surface or joint facing surface 96 and a bone facing surface 98, forming a body 95 therebetween. Joint facing surface 96 and bone facing surface 98 are depicted extending dorsally from body 95 forming dorsal hood 92 therebetween. Bone facing surface 98 is depicted on bone facing side 99. Dorsal hood 92 may, for example, be an elongated extension or appendage from body 95. Dorsal hood 92 is depicted as extending at an angle from interior side 98 of body 95, away from joint facing surface 96. A central post 102 is depicted, extending out form approximately the center of bone facing side 99, having a cylindrical shape and a domed free end. On body 95, bone facing surface 98 may have, for example, a ring 94 extending out from bone facing surface 98, away from joint facing surface 96. Ring 94 may have, for example, an exterior barb 91. Ring 94 may have, for example, an interior opening 94, extending towards joint facing surface 96. Ring 95 may be, for example, concentric with central post 102. A dorsal screw retention hole 100 may, for example, extend from joint facing surface 96 to bone facing surface 98 of dorsal hood 92. Barb 91, may, for example, promote bone fixation.

Figure 7:
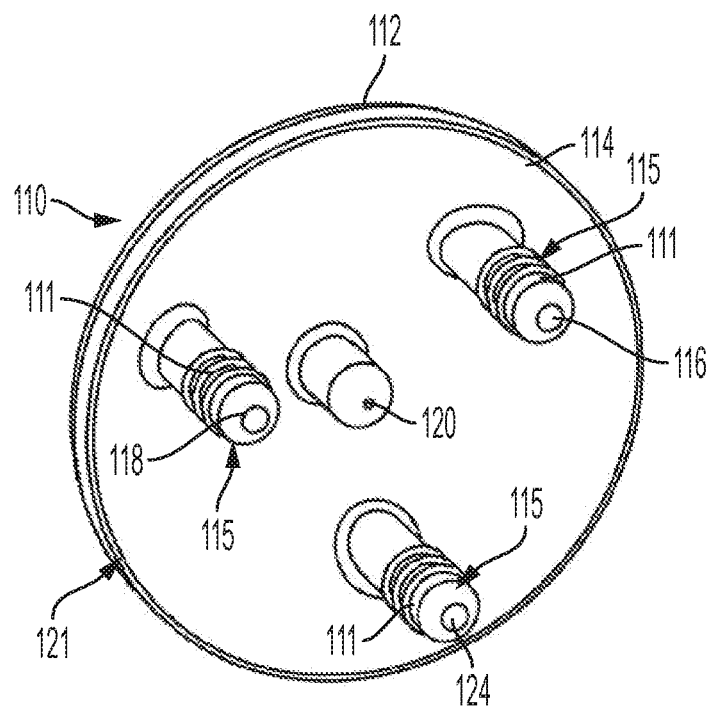
FIG. 7 is a perspective view of a circular post hemiarthroplasty device with an array of barbed posts, in accordance with an aspect of the present invention.

Referring to FIG. 7, another embodiment is depicted as a multi-post hemiarthroplasty device or an implant 110 having an exterior surface or joint facing surface 112 and a bone facing surface 114 forming a body 121 therebetween. Body 121 may be, for example, button-shaped. A central post 120 is depicted, extending out form approximately the center of bone facing surface 114, having a cylindrical shape and a domed free end. A plurality of posts 115 having a cylindrical shape are depicted as having barbed surfaces 111 and extending from bone facing surface 114 and positioned towards the perimeter of body 121. Plurality of posts 115 may include, for example, a first post 116, a second post 124, and a third post 118. Plurality of posts 115 are depicted as having domed shaped free ends. Barbed surfaces 91, may, for example, promote bone fixation.

Figure 8:
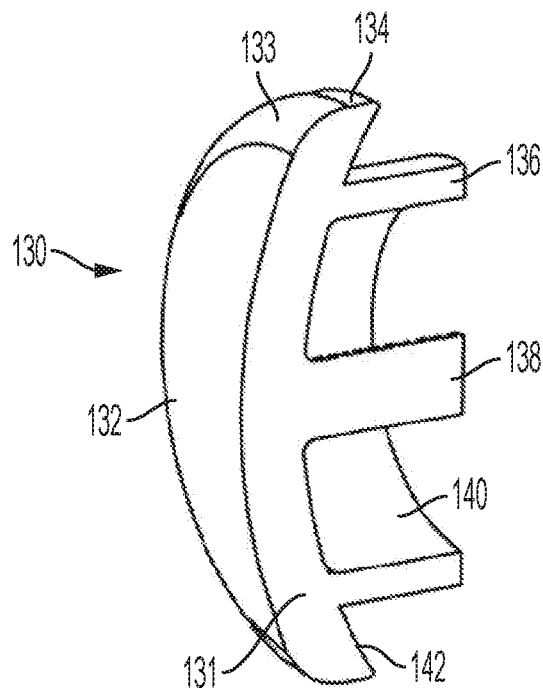
FIG. 8 is a cross-section view of a ring and post hemiarthroplasty device, in accordance with an aspect of the present invention.

Referring to FIG. 8, a still other embodiment is depicted as a cross-section of a ring and post hemiarthroplasty device or an implant 130 having an exterior surface or joint facing surface 132 and a bone facing surface 142 forming a body 131 therebetween. Body 131 may be, for example, button shaped. A central post 138 and a ring 136 are depicted extending out from bone facing surface 142, away from joint facing surface 132. Central post 138 may, for example, extend out from approximately the center of bone facing surface 142 with ring 136 being concentric with central post 138. Central post 138 may have, for example, a cylindrical shape. Joint facing surface 132 may have a tapered region extending towards a circumferential ring 133 around body 131.

Figure 9:
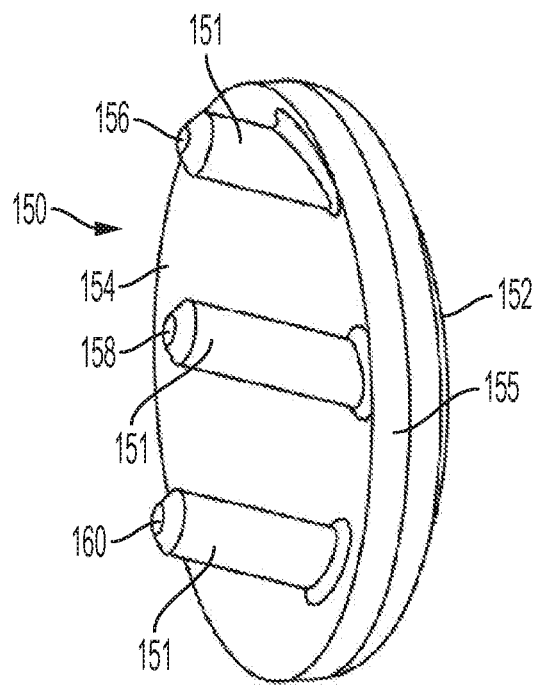
FIG. 9 is a perspective view of a hemiarthroplasty device with oblique posts, in accordance with an aspect of the present invention.

Referring to FIG. 9, yet another embodiment is depicted as a multi-post hemiarthroplasty device or an implant 150 having an exterior surface or joint facing surface 152 and a bone facing surface 154 forming a body 155 therebetween. Body 155 may be, for example, button-shaped. Bone facing surface 154 may be, for example concave, having a plurality of obliquely positioned posts 151 extending out from bone facing surface 154 and having a cylindrical shape. Plurality of posts 151 may include, for example, a first post 156, a second post 158, and a third post 160. Each of plurality of posts 151 may be, for example, have a having a domed or tapered free end.

Figure 10:
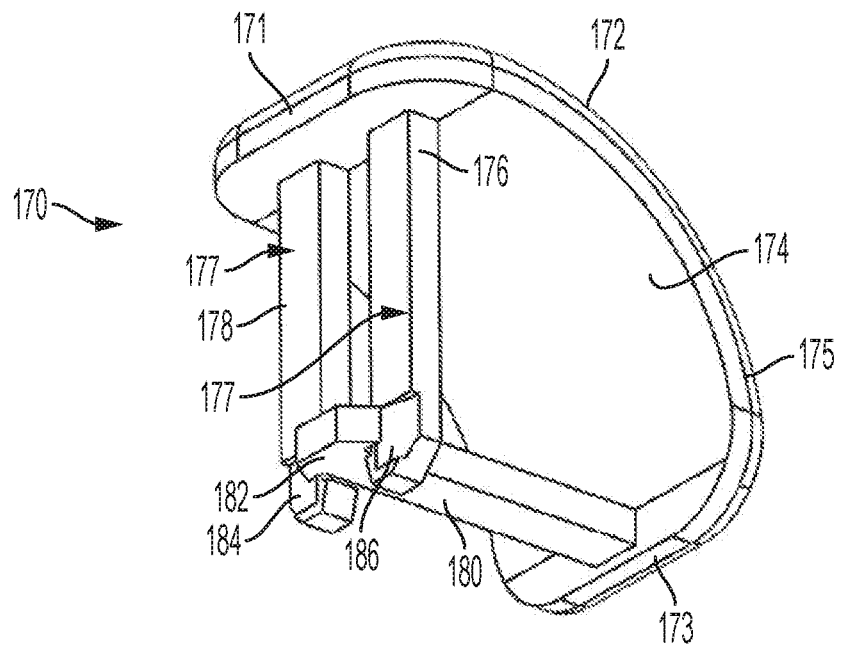
FIG. 10 is a perspective view of a hemiarthroplasty device with cross-retaining posts, in accordance with an aspect of the present invention.

Referring to FIG. 10, a further embodiment is depicted as a crossing retaining post hemiarthroplasty device or an implant 170 having an exterior surface or joint facing surface 172 and a bone facing surface 174 forming a body 175 therebetween. Body 175 is depicted as having a rectangular shape and may have, for example rounded edges. Body 175 may, for example, have a first end 171 and a second end 173 curving towards each other, forming a concave bone facing side 174 and a convex joint facing side 172. A pair of posts 177 (e.g. a first post 176 and a second post 178), positioned towards first end 171 and extending out from bone facing surface 174, are depicted as intersection with a third post 180, positioned towards second end 173 and extending out from bone facing surface 174. The intersection between pair of posts 177 and third post 180, may be perpendicular. First post 176 has a first receiving section 186 and second post 178 has a second receiving section 184. Third post 180 has a barbed free end 182, that is depicted engaging with first receiving section 186 and second receiving section 184, connecting pair of posts 177 with third post 180. First post 176, second post 178, and third post 180 may have a rectangular shape. While a barbed free end 182 is depicted engaging pair of posts 177 and third post, in an alternative embodiment, first post 176 and second post 178, may frictionally engage with third post 180. Body 175 may be elongated between first end 171 and second end 173 and configured (e.g. shaped and dimensioned) for post insertion in a dorsal surface (e.g. pair of posts 177) and an end surface of a bone (e.g. third post 180), covering both the dorsal surface and the end surface of the bone.

Figure 11:
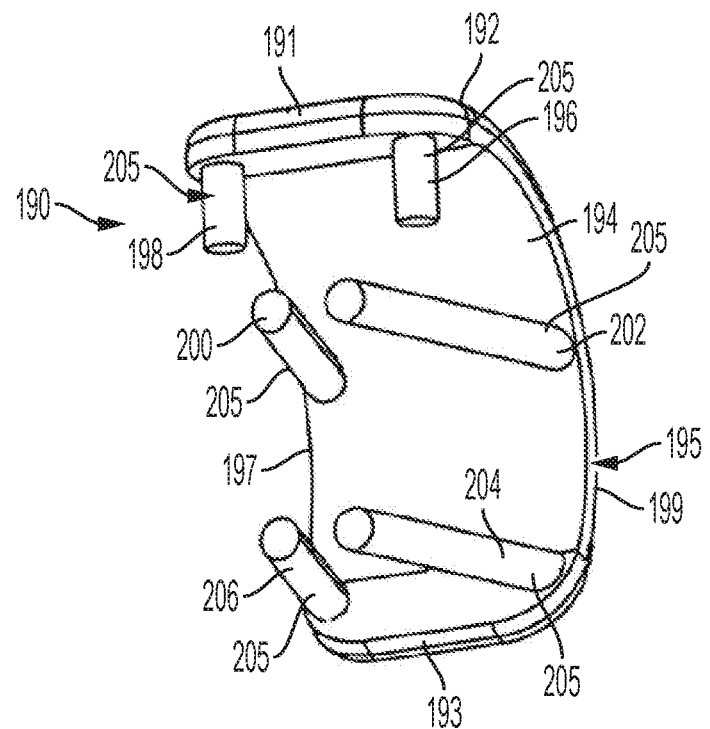
FIG. 11 is a perspective view of a hemiarthroplasty device with canted edge posts, in accordance with an aspect of the present invention.

Referring to FIG. 11, another embodiment is depicted as a canted edge post hemiarthroplasty device or an implant 190 having an exterior surface or joint facing surface 192 and a bone facing surface 194 forming a body 195 therebetween. Body 195 is depicted as having a rectangular shape and may have, for example rounded edges. Body 195 may, for example, have a first end 191 and a second end 193 curving towards each other, forming a concave bone facing side 194 and a convex joint facing side 192. Body 195 may, for example, have a first side 197 and a second side 199. A plurality of posts 205, having a cylindrical shape are depicted as extending from bone facing surface 194, away from joint facing surface 192. Plurality of posts 205 may, for example, be canted or angled extending from bone facing surface 194. Plurality of posts 205 may be, for example, positioned towards the edges of bone facing surface 194. Plurality of posts 205 may, for example, be positioned such that a first post 196 is positioned approximately at first end 191 and second side 199, a second post 198 is positioned approximately at first end 191 and first side 197, a third post 204 is positioned approximately at second end 193 and second side 199, and a fourth post 206 is positioned approximately at second end 193 and first side 197. A fifth post 200 and a sixth post 202 may be, for example positioned between first end 191 and second end 193, with fifth post 200 positioned approximately at first side 197 and sixth post 202 positioned approximately at second side 199. Body 195 may be elongated between first end 191 and second end 193 and configured (e.g. shaped and dimensioned) for post insertion in a dorsal surface and an end surface of a bone, covering both the dorsal surface and the end surface of the bone.

Figure 12:
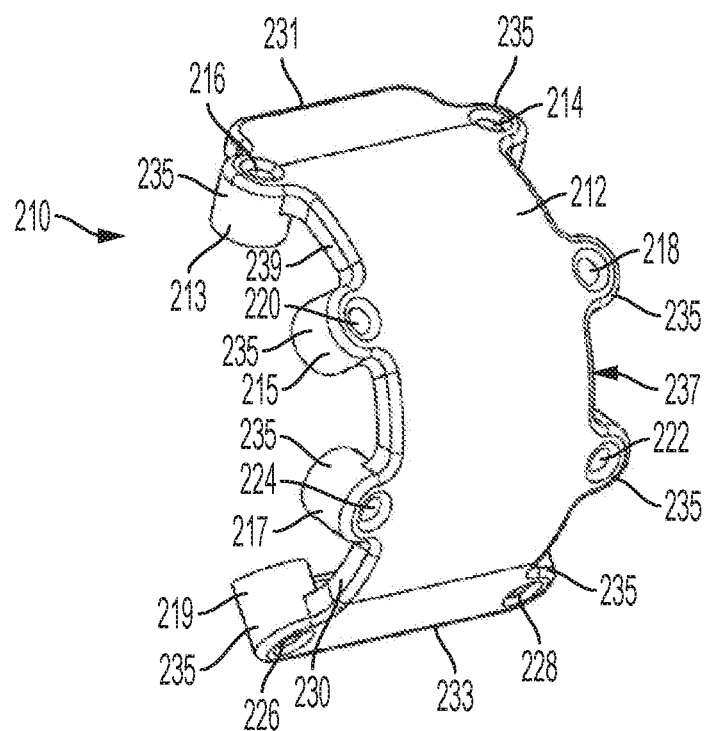
FIG. 12 is a first perspective view of a sheet hemiarthroplasty device with an edge sutured surface, in accordance with an aspect of the present invention.
Figure 13:
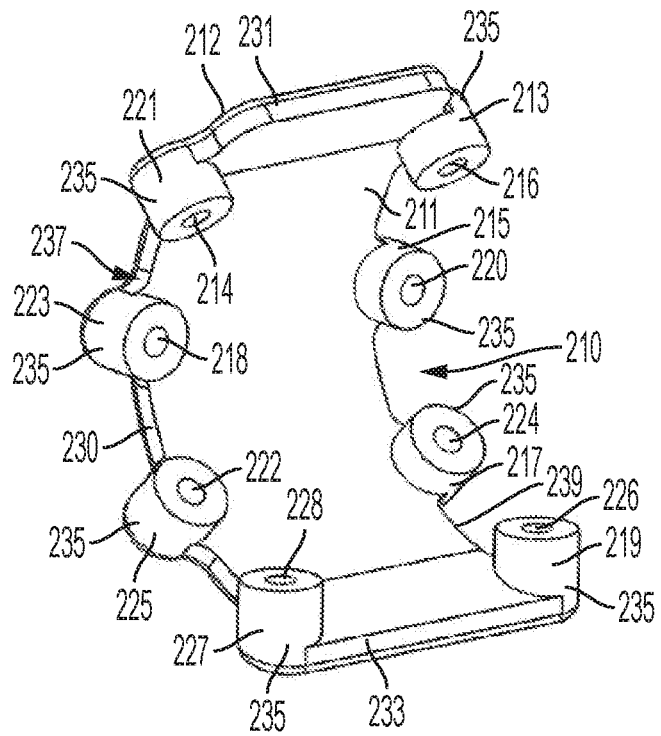
FIG. 13 is a second perspective view of the sheet hemiarthroplasty device of FIG. 12 with an edge sutured surface, in accordance with an aspect of the present invention.
Figure 14:
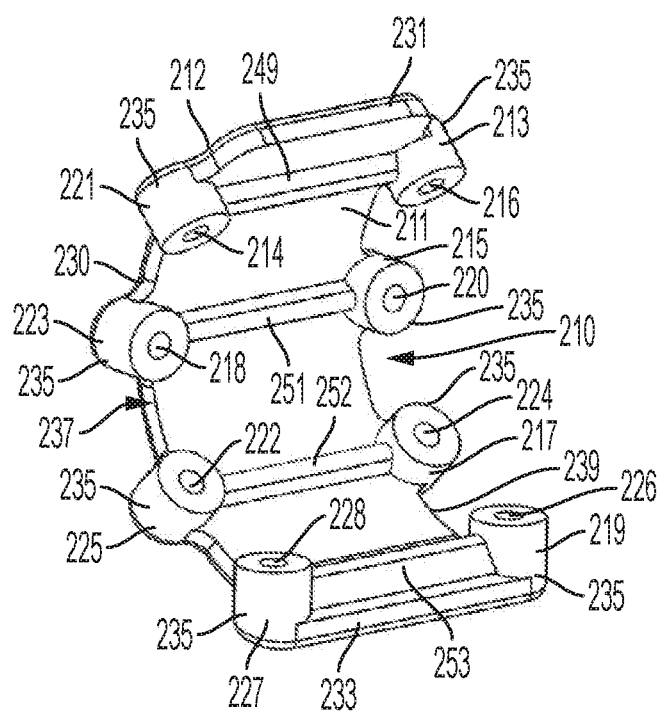
FIG. 14 is a perspective view of the sheet hemiarthroplasty device of FIG. 12 with ribs, in accordance with an aspect of the present invention.

Referring to FIGS. 12-14, a tenth embodiment is depicted as a suture retained hemiarthroplasty device or an implant 210 having an exterior surface or sutured surface or joint facing surface 212 and non-articulating side or a bone facing surface 211 forming a body 230 therebetween. Body 230 is depicted as having a rectangular shape and may have, for example rounded edges. Body 230 may, for example, have a first end 231 and a second end 233 curving towards each other, forming a concave bone facing side 211 and a convex joint facing side 212. Body 230 may, for example, have a first side 237 and a second side 239. A plurality of suture tubes 235, having a cylindrical shape, are depicted as extending from bone facing surface 211, away from joint facing surface 212. Plurality of suture tubes 235 may be, for example, positioned towards the edges of bone facing surface 211. Plurality of suture tubes 235 may, for example, be positioned such that a first suture tube 213 is positioned near first end 231 and at second side 239, a second suture tube 221 is positioned near first end 231 and at first side 237, a third suture tube 219 is positioned at approximately second end 233 and at second side 239, and a fourth suture tube 227 is positioned at approximately second end 233 and at first side 237. A fifth suture tube 223, a sixth suture tube 215, a seventh suture tube 225, and an eighth suture tube 217 may be, for example positioned between first end 231 and second end 233. Fifth suture tube 223 and seventh suture tube 225 may be, for example positioned at first side 237. Sixth suture tube 215 and eighth suture tube 217 may be, for example, positioned at second side 239. Fifth suture tube 223 and sixth suture tube 215 may be, for example, positioned closer to first end 231 and seventh suture tube 225 and eighth suture tube 217 may be, for example, closer to the second end 233.

Still referring to FIGS. 12-14, each of the plurality of suture tubes 235 has a hole extending through. First suture tube 213 has a first hole 216, second suture tube 221 has a second hole 214, third suture tube 219 has a third hole 226, fourth suture tube 227 has a fourth hole 228, fifth suture tube 223 has fifth hole 218, sixth suture tube 215 has a sixth hole 220, seventh suture tube 225 has a seventh hole 222, and eighth suture tube 217 has an eighth hole 224. Body 230 may be elongated between first end 231 and second end 233 and configured (e.g. shaped and dimensioned) for placement on a bone to cover a dorsal surface and an end surface of the bone.

Referring to FIG. 14, the plurality of suture tubes 235 may be connected by transverse. First suture tube 213 and second suture tube 221 may, for example, be connected by a first transverse rib 249. Third suture tube 219 and fourth suture tube 227 may be, for example, connected by a second transverse rib 251. Fifth suture tube 223 and sixth suture tube 215 may be, for example, connected by a third transverse rib 252. Seventh suture tube 225 and eighth suture tube 217 may be, for example, connected with a fourth transverse rib 253. The ribs (e.g. first transverse rib 249, second transverse rib 251, third transverse rib 252, and fourth transverse rib 253) extend out from bone facing surface 211 and away from joint facing surface 212.

Figure 15:
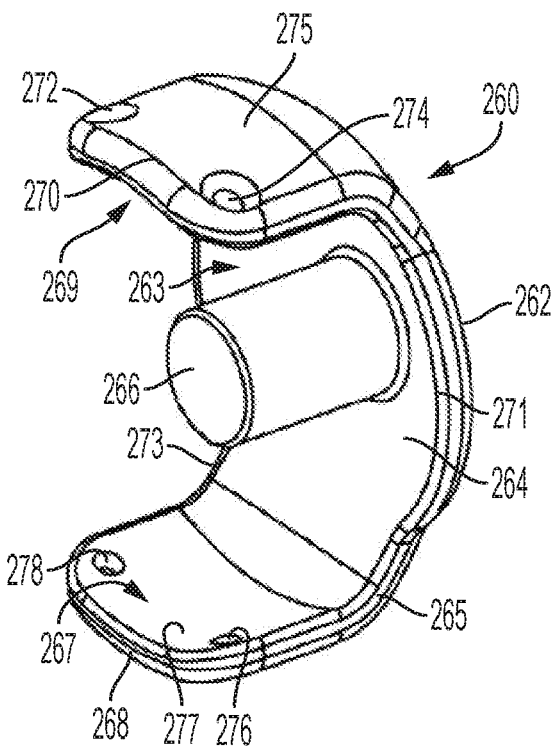
FIG. 15 is a perspective view of a sheet hemiarthroplasty device with suture retention holes, in accordance with an aspect of the present invention.

Referring to FIG. 15, another embodiment is depicted as a suture retained hemiarthroplasty device or an implant 260 having an exterior surface or sutured surface or joint facing surface 262 and non-articulating side or a bone facing surface 264 forming a body 265 therebetween. Body 265 is depicted as having a rectangular shape and may have, for example rounded edges. Joint facing surface 262 and bone facing surface 264 are depicted as having a central circular region 263 and extending dorsally from central circular region 263 of body 265, forming a dorsal region 269 and a dorsal hood 275 therebetween. Joint facing surface 262 and bone facing surface 264 are depicted as extending in a plantar direction from central circular region 263 of body 265, forming a plantar region 267 and forming a plantar hood 277 therebetween. Dorsal hood 275 may, for example, be an elongated extension or appendage from body 265. Plantar hood 277 may, for example, be an elongated extension or appendage from body 265. Dorsal hood 275 and plantar hood 277 are depicted as extending at an angle from bone facing surface 264 of body 265. A central post 82 is depicted, extending out form approximately the center bone facing surface 72 of central circular region 263, and having a cylindrical shape. A first suture hole 272 and a second suture hole 274 are depicted extending from the joint facing surface 262 to the joint facing surface 264 near a first end 270, with first suture hole 272 being positioned near a first side 173 and second suture hole 274 being positioned near a second side 271. A third suture hole 276 and a fourth suture hole 276 are depicted extending from the joint facing surface 262 to the joint facing surface 264 near a second end 268 with third suture hole 276 being positioned near a second side 171 and fourth suture hole 276 being positioned near a first side 273. Body 265 may be configured (e.g. shaped and dimensioned) for post insertion in an end surface of a bone and covering both a dorsal region with dorsal hood 275 and a plantar region with plantar hood 277.

Figure 16:
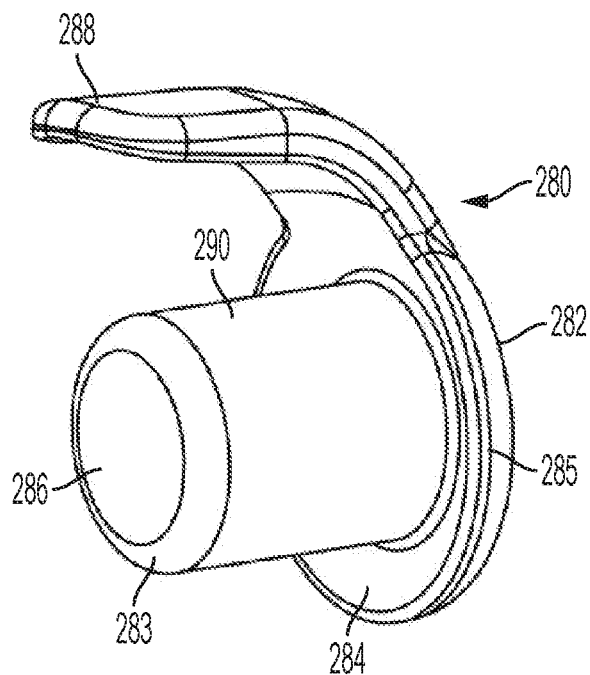
FIG. 16 is a perspective view if a simple post hemiarthroplasty device with an extension, in accordance with an aspect of the present invention.

With reference to FIG. 16, yet another embodiment is depicted as a single post hemiarthroplasty device or an implant 280 having an exterior surface or joint facing surface 282 and a bone facing surface 284 forming a body 285 therebetween. Joint facing surface 282 and bone facing surface 2844 are depicted extending dorsally from body 285 forming a dorsal hood 288 therebetween. Body 285 may, for example, form a button shape. Dorsal hood 288 may also, for example, curve or extend at an angle in the direction of the bone facing surface 284. A post 290, having a cylindrical shape, is depicted extending away from bone facing surface 284 towards a tapered region 283 and a free end 286.

Figure 17:
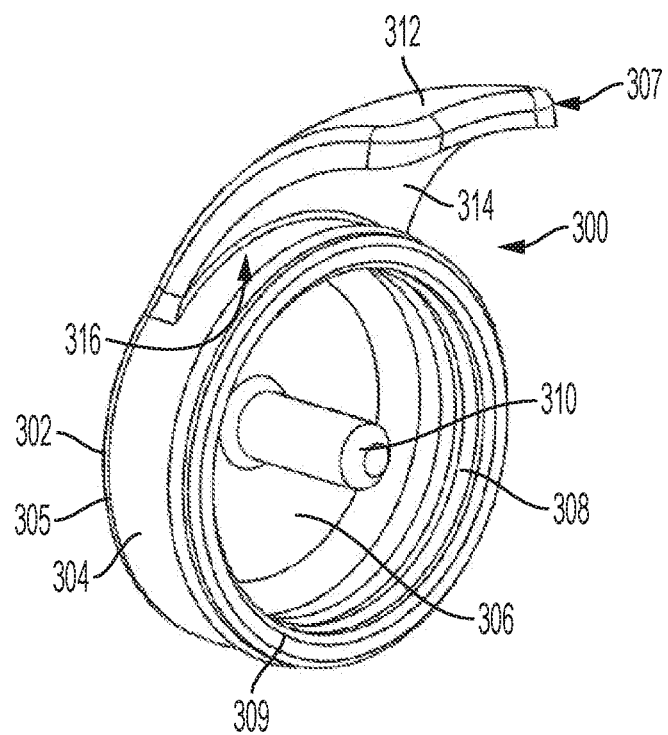
FIG. 17 is a perspective view of a ring hemiarthroplasty device, in accordance with an aspect of the present invention.

With reference to FIG. 17, another embodiment is depicted as a ring hemiarthroplasty device or an implant 300 having an exterior surface or joint facing surface 302 and a bone facing surface 306 forming a body 305 therebetween. Body 305 may be circular, and exterior surface 302 may be planar or concave. A ring 304 extends around the circumference of body 305, and extending out from the bone facing surface 306, away from joint facing surface 302. A dorsal hood 307 is depicted extending from a dorsal region 316 of ring 304. Dorsal hood 307 has a bone facing surface 314 and an exterior surface 312, with dorsal hood 307 curving dorsally in the direction of bone facing surface 314. Ring 304 is depicted as concentric with a post 310 extending from the approximate center of bone facing surface 306, away from joint facing surface 302. Post 310 may be cylindrical with a tapered free end. Ring 304 may have a barbed region 308 at a free end 309. Barbed region 308, may, for example, promote bone fixation.

Figure 18:
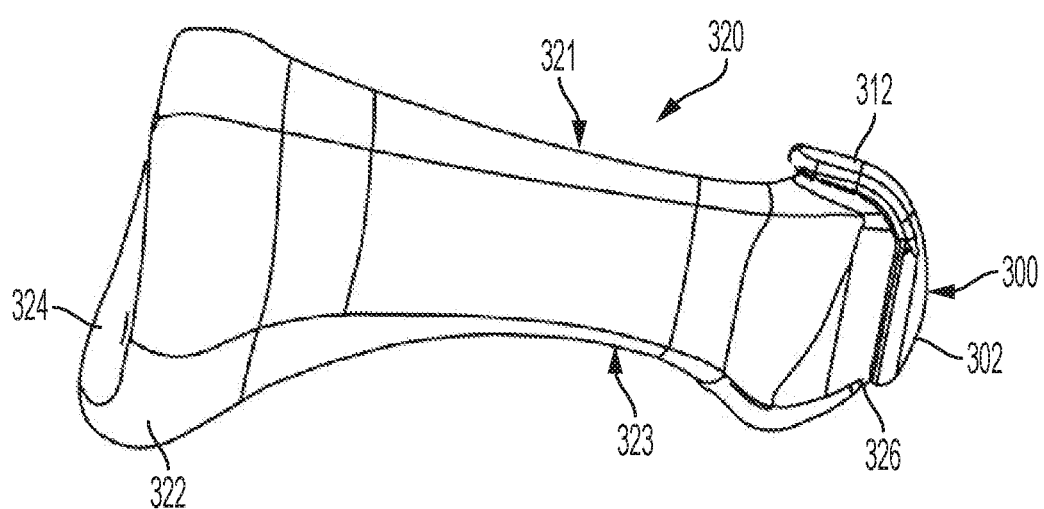
FIG. 18 is a first perspective view a metatarsal bone with an articulating button hemiarthroplasty device, in accordance with an aspect of the present invention.
Figure 19:
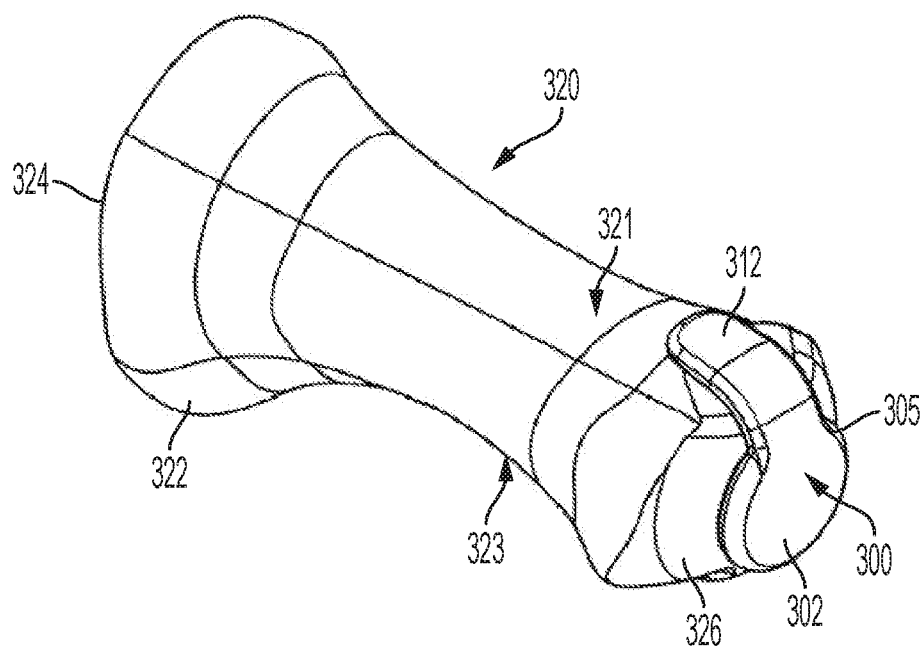
FIG. 19 is a second perspective view of the metatarsal bone of FIG. 18 with an articulating hemiarthroplasty device, in accordance with an aspect of the present invention.
Figure 20:
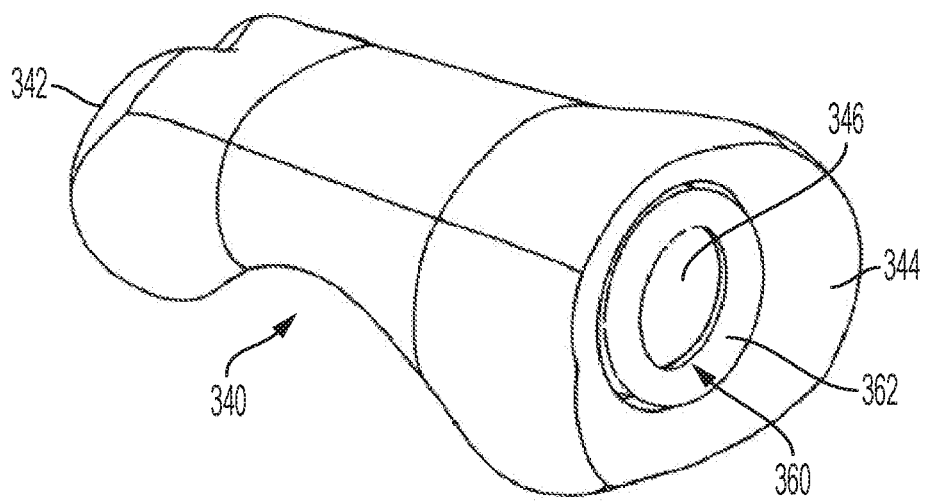
FIG. 20 is a perspective view of a phalangeal bone with an articulating element hemiarthroplasty device, in accordance with an aspect of the present invention.

With reference to FIGS. 17-19, a metatarsal bone 320 is depicted with the articulating ring hemiarthroplasty device 300 engaged with a phalangeal end or metatarsal head 326. Metatarsal bone 320 has a tarsometatarsal end 324, a bone surface 322, a dorsal surface 321, and a plantar surface 323. Ring hemiarthroplasty device 300 may have, for example, a body region 305, in particular ring 304 and bone facing surface 306, engaged with metatarsal head 326. Ring hemiarthroplasty device 300 may also have, for example, an articular dorsal region 312, engaged with dorsal phalangeal end of bone surface 322. Joint facing surface 302, faces away from metatarsal head 326 for engagement with a phalange.

Figure 21:
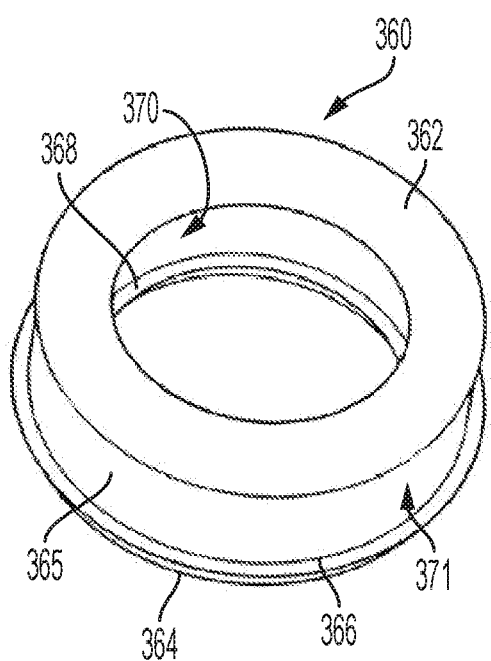
FIG. 21 is a perspective view of an open-faced ring hemiarthroplasty device, in accordance with an aspect of the present invention.
Figure 22:
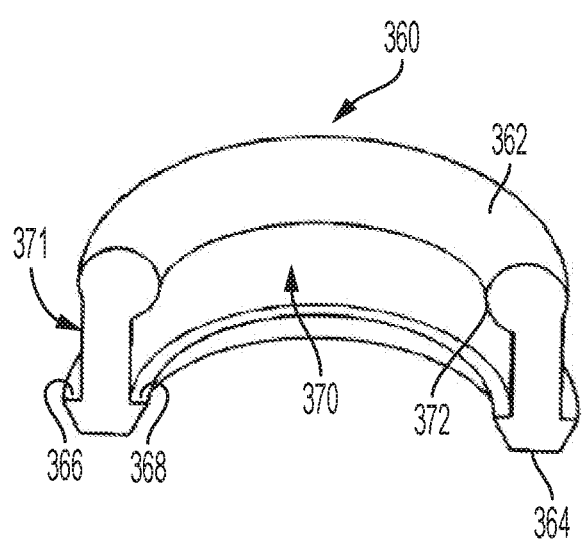
FIG. 22 is a cross-section view of the open-faced ring hemiarthroplasty device, in accordance with an aspect of the present invention.

With reference to FIG. 20-22, a phalange 340 is depicted having an anterior end 342 and a metatarsal end 344. An articulating ring hemiarthroplasty device or an implant 360 is depicted as being engaged with phalange 340 at metatarsal end 344. Ring 360 is depicted as having an outer surface 362 extending out from metatarsal end 344. Also depicted is a central open region 346 of ring 360 with bone exposed. Outer surface 362 may be configured (e.g. shaped and dimensioned) for contact with a metatarsal head (e.g. metatarsal head 326).

With reference to FIGS. 17-22, one or both joints may have an implant (e.g. implant 300 and/or implant 360), with the respective joint facing sides of the implants (e.g. 302 and 362) facing each other. With reference to implant 300, the joint facing side may be configured (e.g. shapes and dimensioned) for contact with a partial joint member (not shown) or the metatarsal facing end 344 of phalange 340. In some embodiments, metatarsal facing end 344 of phalange 340 may have a metal cap (not shown) for engagement with joint facing surface 302 of implant 300.

With reference to FIGS. 21 and 22, articulating ring hemiarthroplasty device 360 is depicted having an exterior surface or joint facing surface 362 and a bone facing surface 364 forming a ring 365, therebetween. Ring 365 further is depicted with an inner surface 370 and an outer surface 371. The bone facing surface 364 has an exterior barbed end 366 extending from outer surface 371, and an interior barbed end 368, extending from inner surface 370. Joint facing surface 362 may have a tubed region 372 extending along joint facing surface 362. Exterior barded end 366 and interior barbed end 368, may, for example, promote bone fixation.

Figure 23:
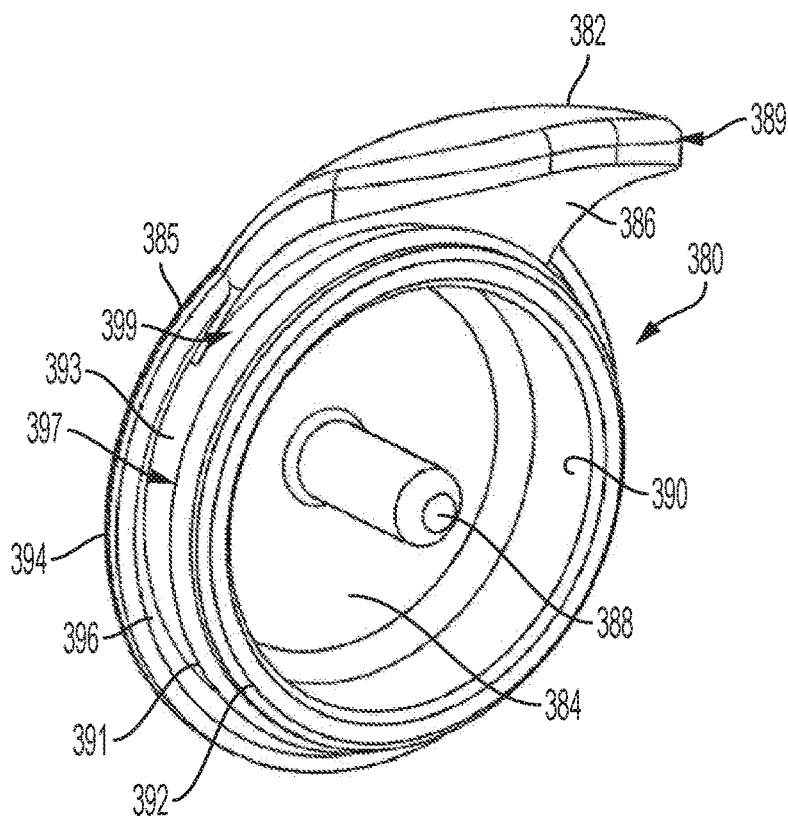
FIG. 23 is a perspective view of a ring hemiarthroplasty device with an exposed shoulder, in accordance with an aspect of the present invention.
Figure 24:
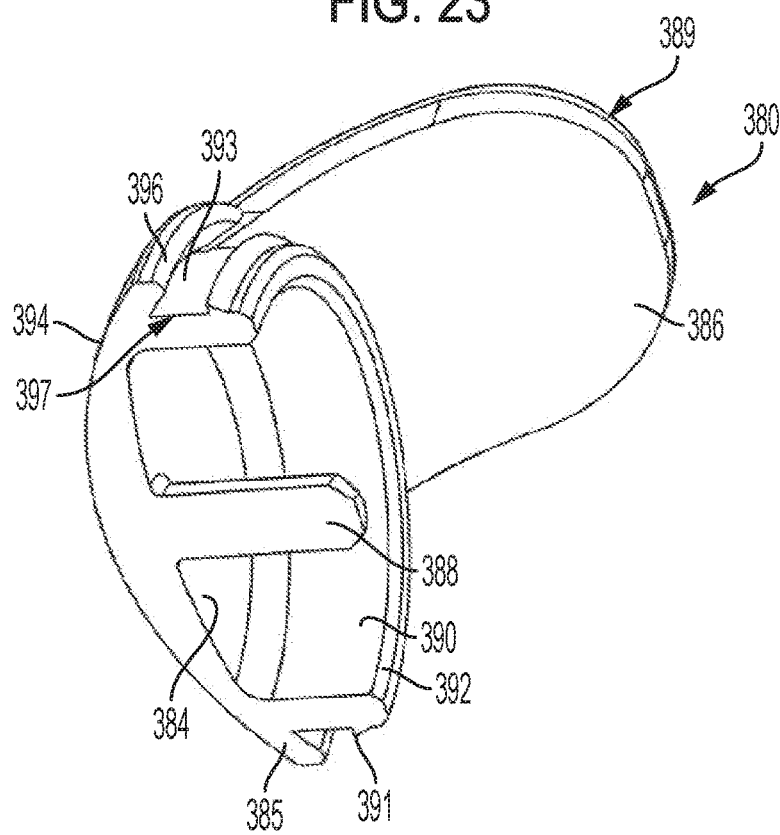
FIG. 24 is a cross-section view of the ring hemiarthroplasty device of FIG. 23 with an exposed shoulder, in accordance with an aspect of the present invention.

With reference to FIGS. 23 and 24, an embodiment is depicted as a ring hemiarthroplasty device or an implant 380 having an exterior surface or joint facing surface 394 and a bone facing surface 384 forming a body 385 therebetween. A ring 393, having an inner surface 390 and an outer surface 397, extends out from the bone facing surface 384 to a free end 392. Free end 392, may have, for example a barb 391 extending from outer surface 397. Ring 393 is depicted as being inset from the perimeter of body 385, forming an inset region 396 between the perimeter of body 385 and ring 393. Joint facing surface 394 is depicted as being convex, with inset region 396 following the convex curvature. Bone facing surface 384 within ring 393 may be, for example, planar. A dorsal hood 389 is depicted extending from a dorsal region 399 between body perimeter and ring 393. Dorsal hood 389 has a bone facing surface 386 and an exterior surface 382, with dorsal hood 389 curving dorsally in the direction of bone facing surface 386. Ring 393 is depicted as concentric with a post 388 extending from the approximate center of bone facing surface 384, away from joint facing surface 394. Post 388 may be cylindrical with a tapered free end extending past the free end 392 of ring 393. Barb 391, may, for example, promote bone fixation.

Figure 25:
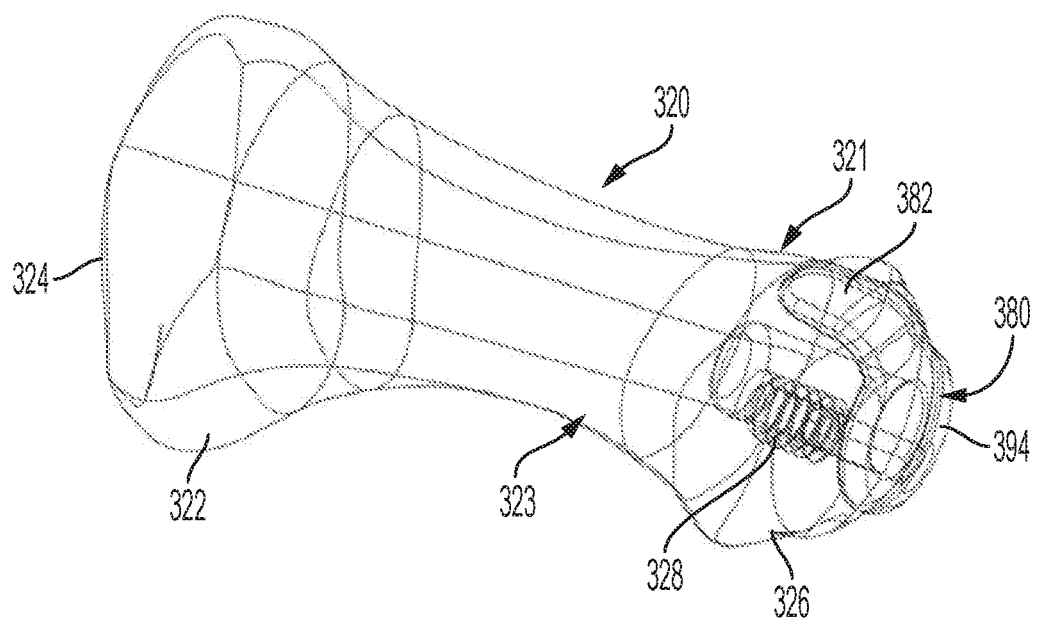
FIG. 25 is a perspective cut-away view of the metatarsal bone of FIG. 18 with an articulating button hemiarthroplasty device, in accordance with an aspect of the present invention.
Figure 26:
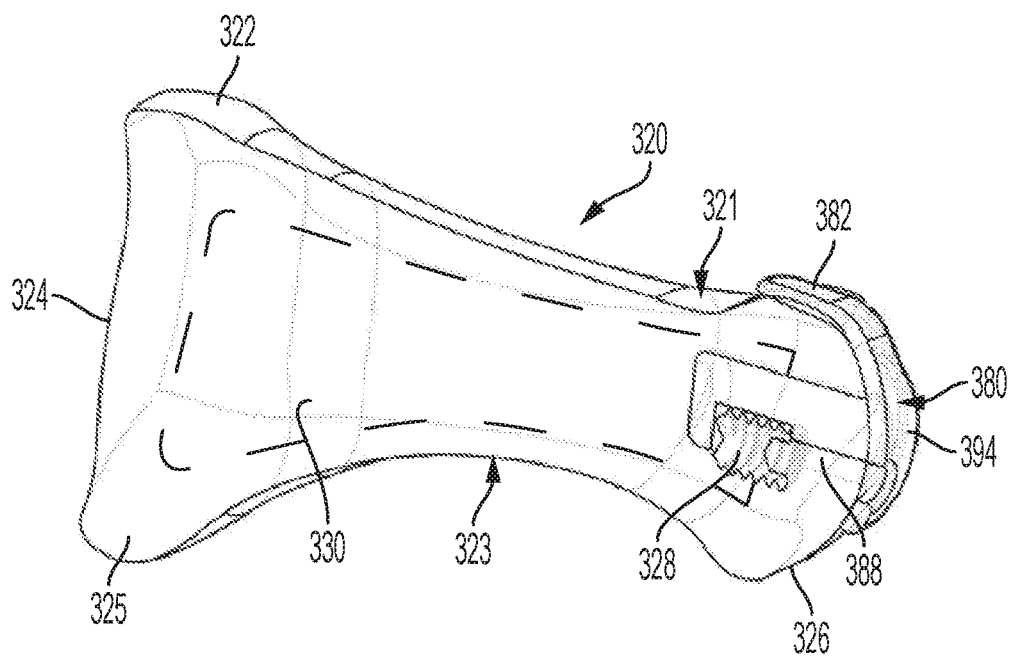
FIG. 26 is a cross-section view of the metatarsal bone of FIG. 18 with an articulating button hemiarthroplasty device, in accordance with an aspect of the present invention.

With reference to FIGS. 25 and 26, metatarsal bone 320 is depicted with implant 380 connected at metatarsal head 326. A screw plug 328 is depicted as having been inserted into metatarsal head 326, with screw plug providing retention for post 388. Dorsal hood 382 has been placed onto and engaged with the dorsal phalangeal end of bone surface 322.

With reference to FIG. 26, screw plug 328 is depicted as being within a cancellous bone region 330. Only a small segment of post 388 is depicted within the cancellous region 330 with the remainder of the implant 388, including, for example, the bone facing surface 384 positioned against a cortical bone region 325. The cancellous bone region 330 is a soft interior bone region within an exterior hard cortical bone region 325. A bone surfaces (e.g. bone surface 322) is cortical bone.

Figure 27:
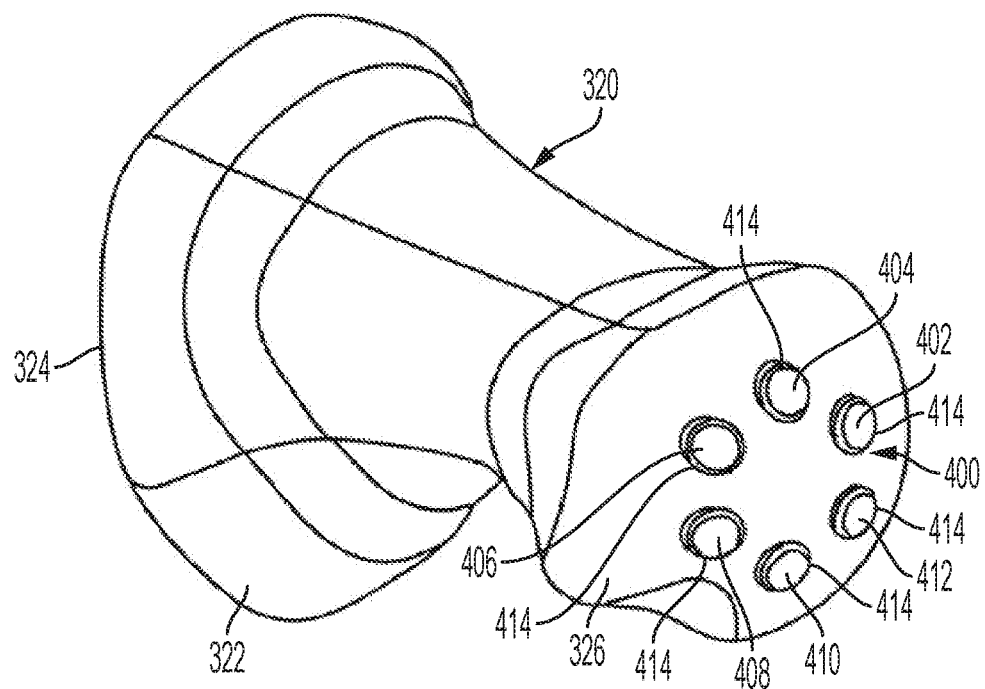
FIG. 27 is a perspective view of the metatarsal bone of FIG. 18 with an embedded segmental articulating hemiarthroplasty device, in accordance with an aspect of the present invention.
Figure 30:
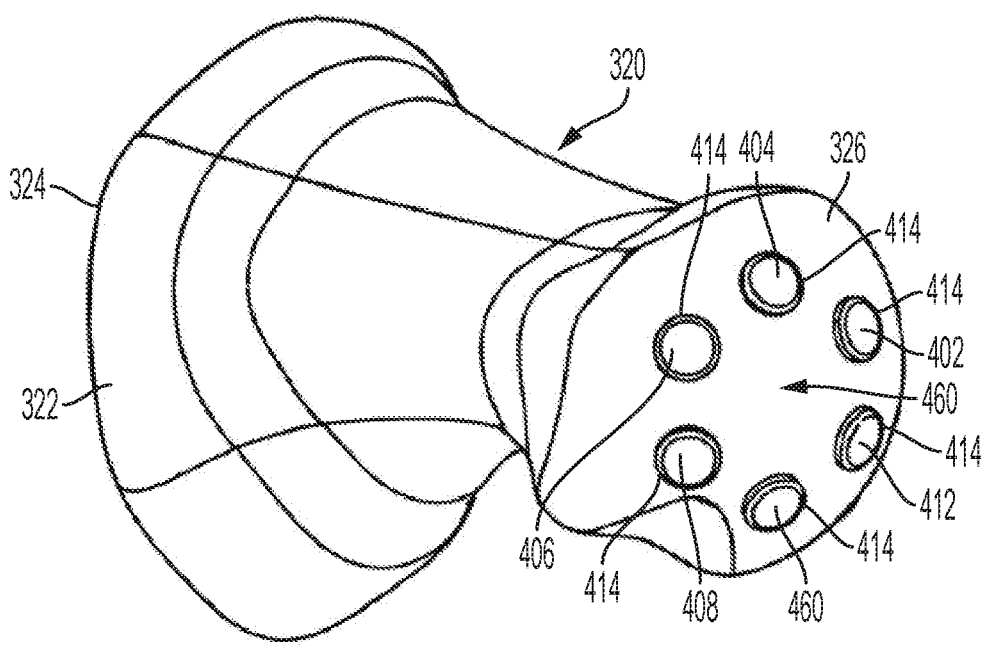
FIG. 30 is a perspective view of the metatarsal bone of FIG. 18 with an embedded splayed axis segmental articulating hemiarthroplasty device, in accordance with an aspect of the present invention.
Figure 31:
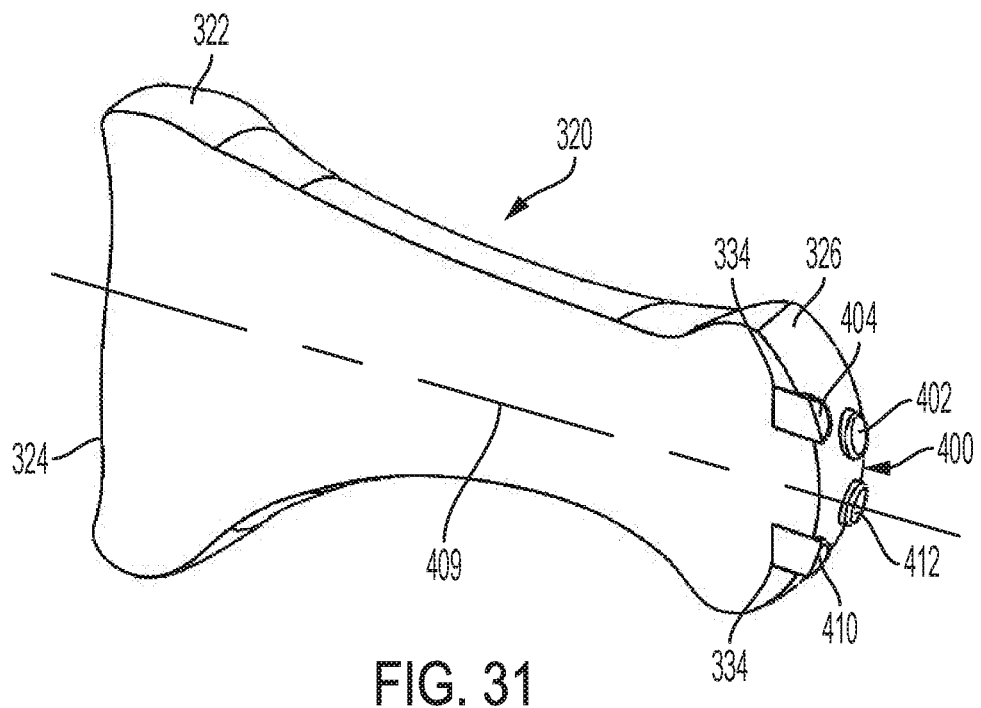
FIG. 31 is a perspective cross-section view of the metatarsal bone of FIG. 18 with an embedded segmental articulating hemiarthroplasty device, in accordance with an aspect of the present invention.
Figure 32:
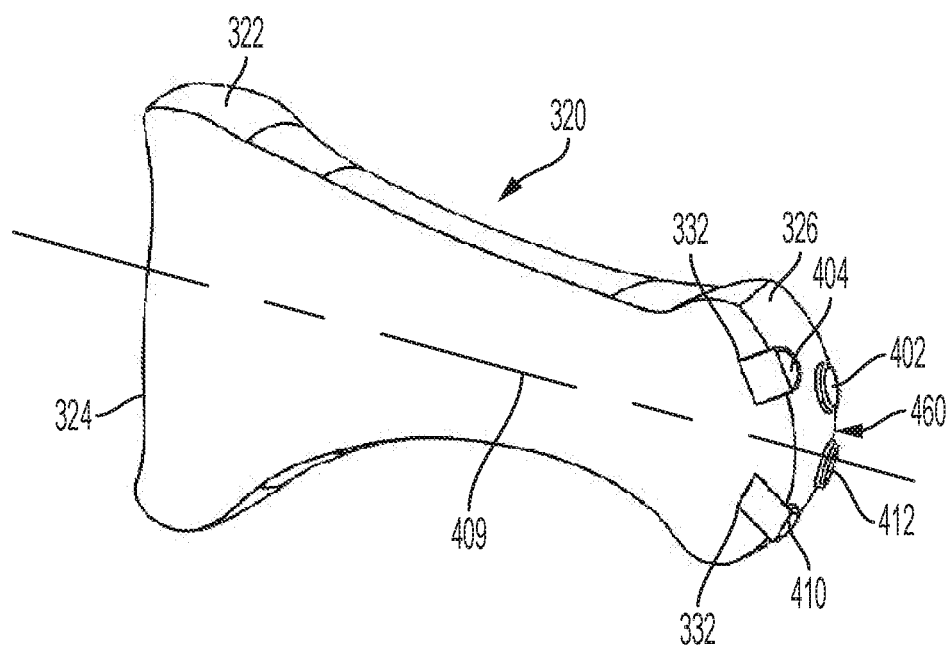
FIG. 32 is a perspective cross-section view of the metatarsal bone of FIG. 18 with an embedded splayed axis segmental articulating hemiarthroplasty device, in accordance with an aspect of the present invention.

With reference to FIGS. 27 and 30-32, an embodiment of a segmented hemiarthroplasty device or an implant 400 and a segmented hemiarthroplasty device or an implant 460 are depicted inserted into the metatarsal head 326 of metatarsal bone 320. With reference to FIGS. 27 and 31, implant 400 includes a plurality of plugs or articulating elements 414, for example, a first plug 402, a second plug 404, a third plug 406, a fourth plug 408, a fifth plug 410, and a sixth plug 412 inserted into holes 334 and disposed on metatarsal head 326 in a circular formation. Holes 334 are, for example, longitudinally disposed and approximately parallel with an anterior/posterior longitudinal axis 409. With reference to FIGS. 30 and 32, plurality of plugs or articulating elements 414 of implant 460 are the same as those of implant 400 and will not be repeated for the sake of brevity. For implant 460, first plug 402, second plug 404, third plug 406, fourth plug 408, fifth plug 410, and sixth plug 412 are depicted as disposed on metatarsal head 326 in a circular formation in holes 332 in a splayed axis formation and angled towards anterior/posterior longitudinal axis 409. Holes 332 and holes 334 may be, for example, positioned entirely within a cortical region (not shown) of metatarsal bone 320 such that plurality of plugs 414 do not extend into a cancellous region (not shown) of metatarsal bone 320. Plurality of plugs 414 are also depicted as having a portion extending out from metatarsal head 326.

Figure 28:
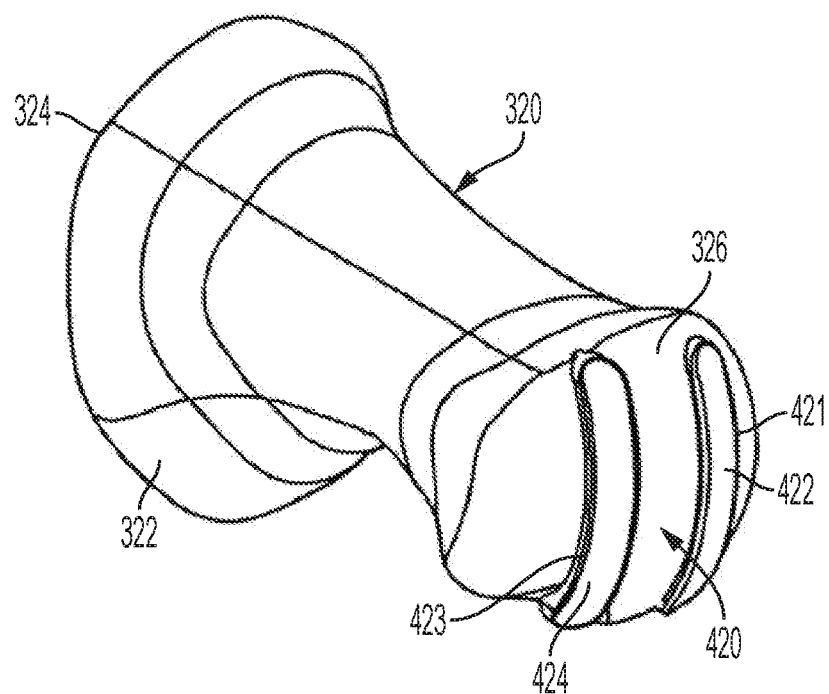
FIG. 28 is a perspective view of the metatarsal bone of FIG. 18 with an embedded twin linear articular surfaces hemiarthroplasty device, in accordance with an aspect of the present invention.

With reference to FIG. 28, an embodiment of a twin linear segmented hemiarthroplasty device or an implant 420 is depicted as having two linear strips, for example, first strip 422 disposed in groove 421 and second strip 424 disposed in groove 423 on metatarsal head 326 of metatarsal bone 320. Groove 421 and groove 423 may be, for example, parallel to each other and be within the cortical region (not shown) of metatarsal bone 320. A portion of first strip 422 and second strip 424 are depicted as extending out from metatarsal head 326.

Figure 29:
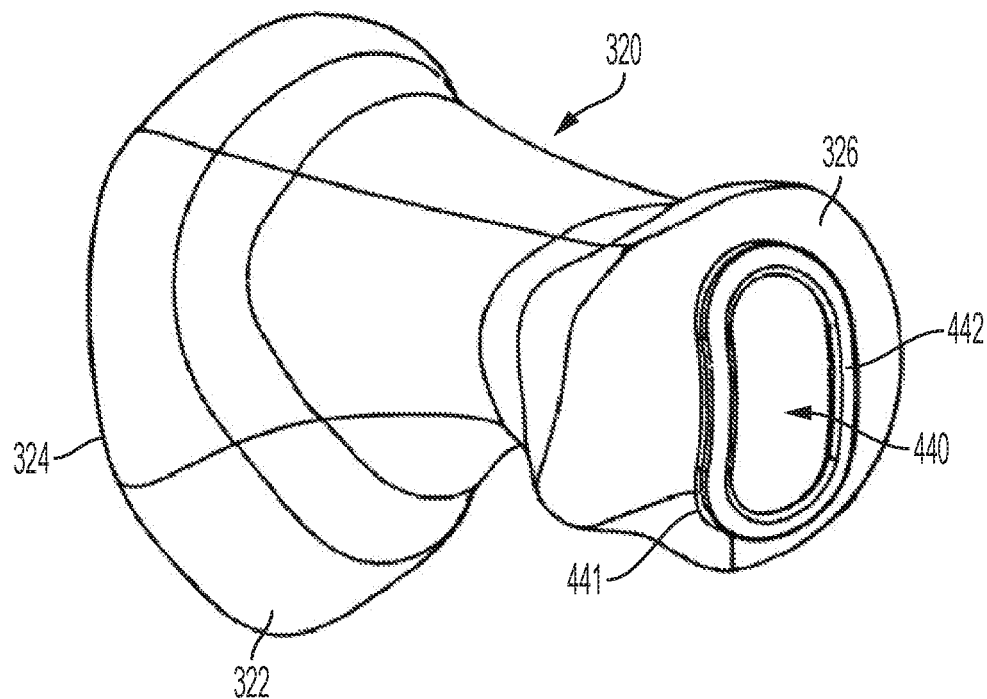
FIG. 29 is a perspective view of the metatarsal bone of FIG. 18 with an embedded ovular ring, in accordance with an aspect of the present invention.

With reference to FIG. 29, an embodiment of an ovular ring hemiarthroplasty device or an implant 440 is depicted as an ovular ring 442 disposed within a groove 441 on metatarsal head 326. Groove 441 may be, for example, fully within a cortical bone region (not shown) of metatarsal bone 320. Ovular ring 442, is depicted as extending out for metatarsal head 326.

With reference to FIGS. 18, 19, and 27-32, the positioning of implants (e.g. implant 300, implant 380, implant 400, implant 420, implant 440, and implant 460) on metatarsal head may, for example, depend on the size of the bones of a patient (e.g. metatarsal bone 320), the metatarsal bone (e.g. first metatarsal bone) being repaired, joint degeneration, bone degeneration, and bone positioning relative to other bones (e.g. metatarsal bone 320 relative to phalange 340).

Figure 33:
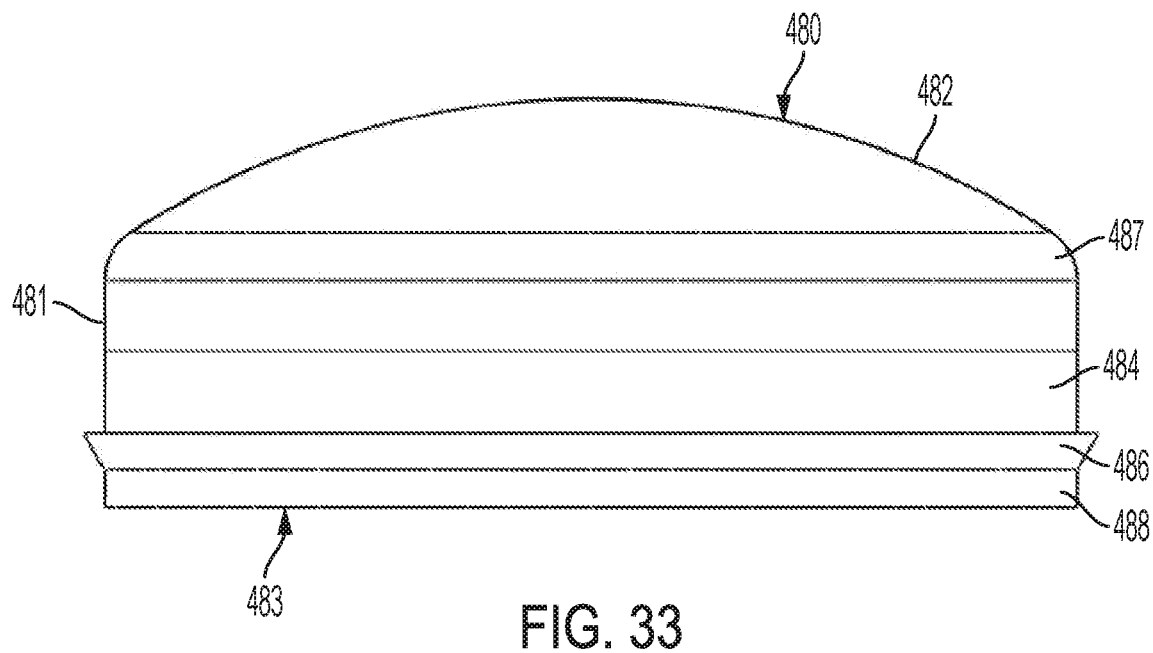
FIG. 33 is a side perspective view of a barbed based ring hemiarthroplasty device, in accordance with an aspect of the present invention.

With reference to FIG. 33, an embodiment of a cap hemiarthroplasty device or an implant 480 is depicted as having a domed region 482 and a sidewall 481 connected by a rounded region 487. Sidewall 481 extends out from and along the circumference of rounded region 487 to a base region 488. A reinforcing band 484 is depicted around the circumference of sidewall 481 extending to a barbed region 486, with barbed region 486 being connected to base region 488. Sidewall 481, reinforcing band 484, barbed region 486, and base region 488 form a ring with an opening 483 opposite domed region 482. Opening 483 may, for example, extend from base region 488 to an underside of domed region 482. Base region 488, barbed region 486, and reinforcing ban 484 may be, for example, fabricated from a metal, or a polymer coated metal. Domed region 482, rounded region 487, and sidewall 481 may be, for example, fabricated from a polymer or a polymer coated metal. Barbed region 486, may, for example, promote bone fixation.

Figure 34:
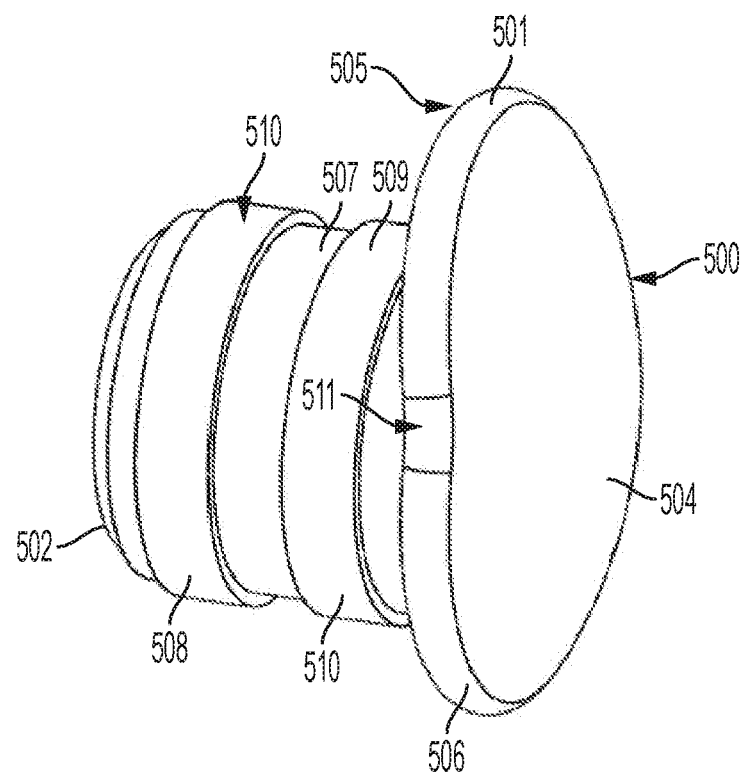
FIG. 34 is a perspective view of a post, in accordance with an aspect of the present invention.

With reference to FIG. 34, an embodiment of a post hemiarthroplasty device or an implant 500, having a post 507 extending from a cap 501. Post 507 may have, for example a plurality of barbs 510, for example, first bard 509 and second barb 508, extending out from the circumference of post 507. Cap 501 may have, for example, a dome or exterior region 504 extending to a perimeter base ring 506 around the base of dome 504. Cap 501 may further have a bone facing surface 505 from which post 507 extends. Bone facing surface 505 may, for example, be a planar surface extending from base ring 506 in towards post 507 or bone facing surface 505 may be concave extending towards dome 504 from base ring 506 towards post 507. Dome 504 and base ring 506 may not, for example, not be circular, having an indented region 511 on base ring 506. Post 507 is depicted as having a tapered free end 502. Plurality of barbs 510, may, for example, promote bone fixation.

Figure 35:
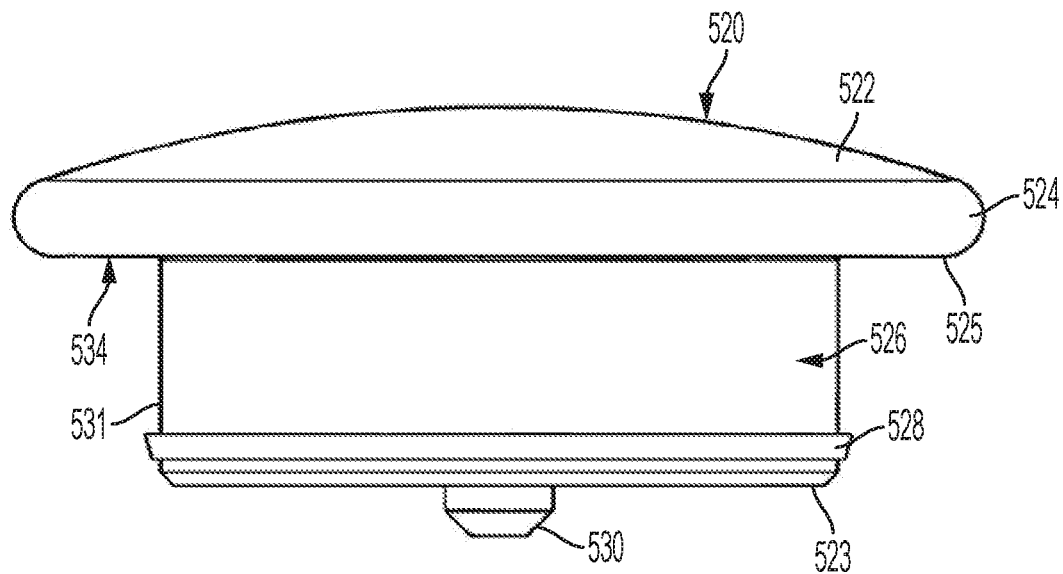
FIG. 35 is a side perspective view of a barbed based ring hemiarthroplasty device with a central ring, in accordance with an aspect of the present invention.
Figure 36:
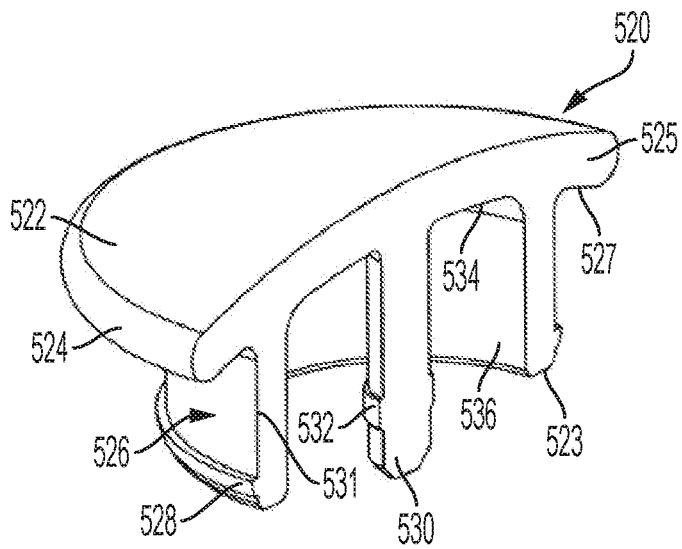
FIG. 36 is a perspective cross-section view of the barbed based ring hemiarthroplasty device of FIG. 33, in accordance with an aspect of the present invention.
Figure 37:
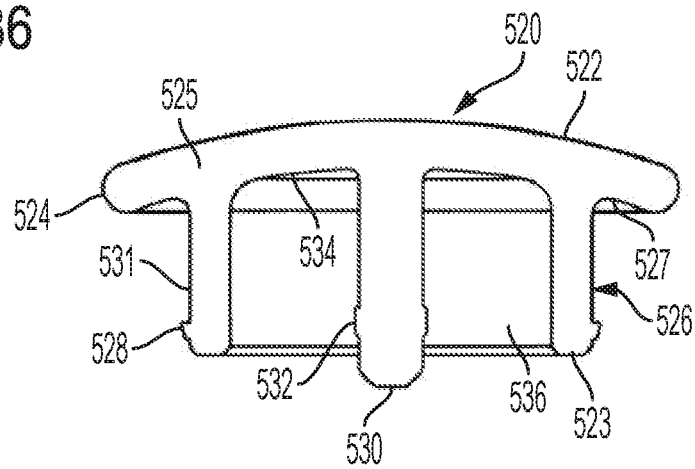
FIG. 37 is a side perspective cross-section view of the barbed based ring hemiarthroplasty device of FIG. 33, in accordance with an aspect of the present invention.

With reference to FIGS. 35-37, an embodiment is depicted as a ring hemiarthroplasty device or an implant 520 having an exterior surface or joint facing surface 522 and a bone facing surface 534 forming a body 525 therebetween. Joint facing surface 522 and bone facing surface 534 are joined by a circumferential ring 524. A ring 526, having an inner surface 536 and an outer surface 531, extends out from the bone facing surface 534 to a free end 523. Free end 523, may have, for example a barb 528 extending from outer surface 531, away from joint facing surface 522. Ring 526 is depicted as being inset from the perimeter of body 525, forming an inset region 527 between the circumferential ring 524 around the perimeter of body 525 and ring 526. Joint facing surface 534 is depicted as being convex, with inset region 527 following the convex curvature. Bone facing surface 534 within ring 526 may be, for example, convex and following the curvature of inset region 527. Ring 526 is depicted as approximately concentric with a post 530 extending from the approximate center of bone facing surface 534, away from joint facing surface 522. Post 530 is depicted as cylindrical with a barb 532 and a tapered free end, extending past free end 523 of ring 524. Barb 532 and barb 528, may, for example, promote bone fixation.

Figure 38:
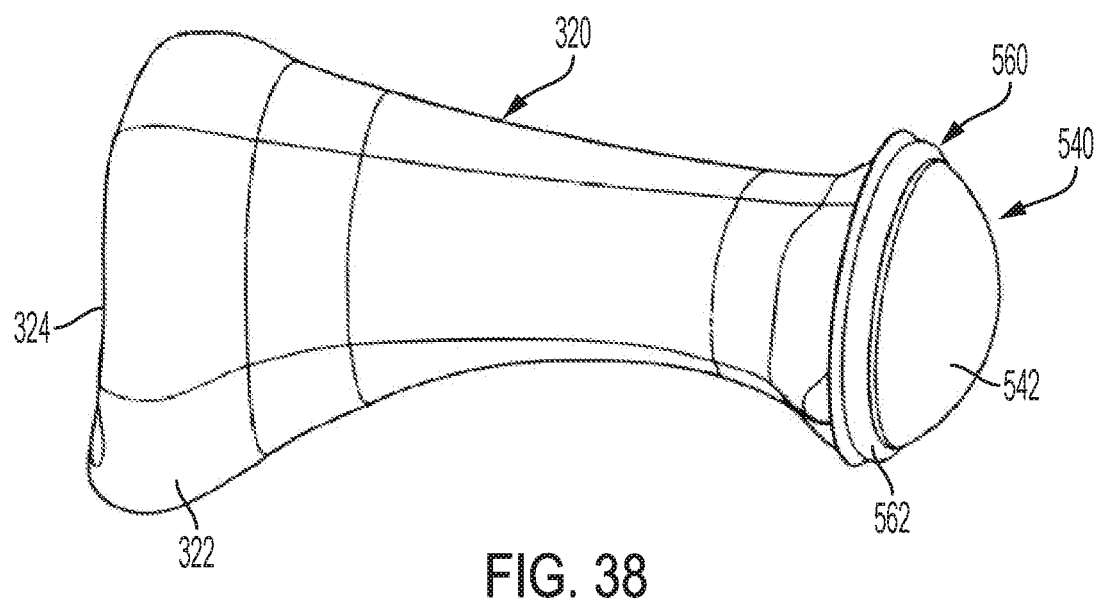
FIG. 38 is a side perspective view of the metatarsal bone of FIG. 18 with a sheet and annular ring hemiarthroplasty device, in accordance with an aspect of the present invention.
Figure 39:
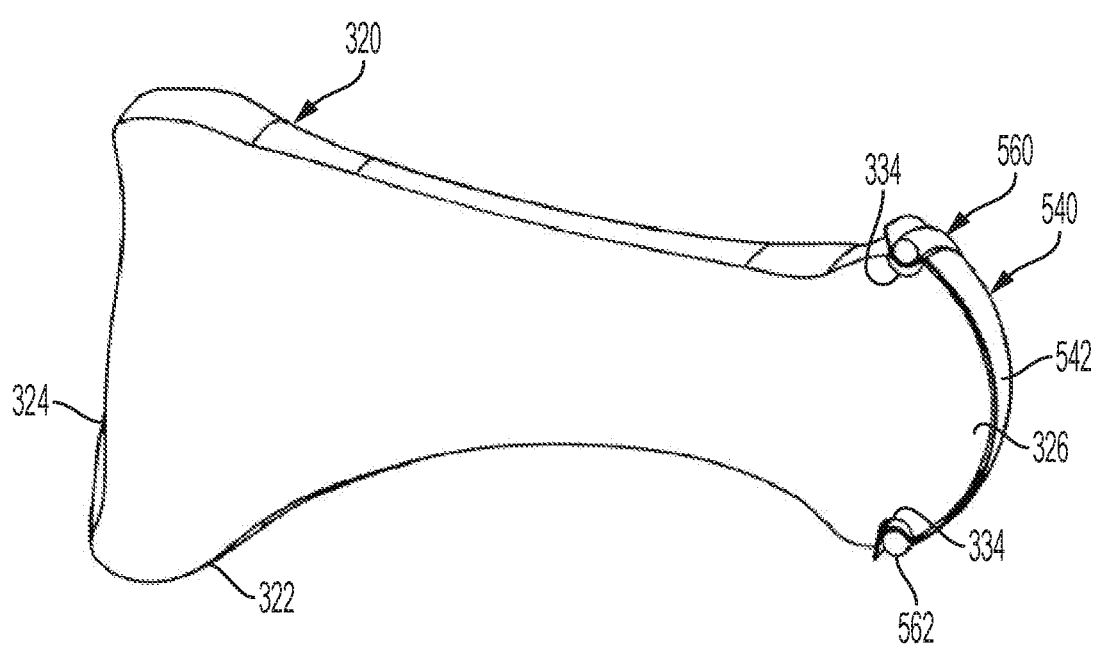
FIG. 39 is a cross-section side perspective view of the metatarsal bone of FIG. 18 with a sheet and annular device, in accordance with an aspect of the present invention.

With reference to FIGS. 38 and 39, an embodiment is depicted as an annular ring hemiarthroplasty device or an implant 560 surrounding a cover 540 affixed to metatarsal head 326 of metatarsal bone 320. An annular groove 334 is depicted surrounding metatarsal head 326. A sheet 542 is depicted as positioned over metatarsal head 326 and extending over annular groove 334. Annular ring 562 is depicted as positioned within annular groove 334, providing retention for sheet 542 and providing for cover 540 over metatarsal head 326. Annular groove, 334 may be, for example, wholly made within a cortical bone region.

With reference to FIGS. 40 and 41 a cup shaped cannulated reamer 580 and a machined metatarsal head 326 of metatarsal bone 320 is depicted. With reference to FIG. 40, reamer 580 is shown first cup members 588 having open region 581 and open region 583 separating first cup member 588, with first cup member 588 surrounding a cup base 587 with a canular opening 587, extending into a tube 582. Second cup members 590 extend out and away from first cup members 588. First cup member 588, cup base 587, canular opening 586, and second cup members 590 are depicted forming an operative end 592 of reamer 580. Tube 582 extend away from operative end 592 of reamer 580. Reamer 588 may, for example, be rotated to machine a bone.

With reference to FIGS. 40 and 41, operative end 592 of reamer 580 may be positioned facing and moved towards metatarsal head 326. First cup members 588 may, for example, create a ring shaped hole 337 around a cylindrical region 336. The surface of region 336 may be smoothed contact with the cup base 587. Second cup members 590 may provide, for example, additional machining to metatarsal head 326, preparing the surface 338 for implant insertion and interaction with a phalange. Canular opening 586 may, for example, remove bone debris or it may be used to support the reamer 580 on a k-wire (not shown) inserted into the bone. Reamer 580, may for example, provide for cortical bone machining, with only cup members 588 forming ring shaped hole 337 into metatarsal head 326. Ring shaped hole 337 may, for example, extend only into cortical bone, with cortical bone being the region of metatarsal bone 320 extending from the surface 322 inwards to the cancellous bone region (not shown). However, remaining within the cortical bone region may depend on the health of the metatarsal head 326 and the joint (not shown). Machining may, for example, be required into the cancellous region of bone. However, the process of using the cup reamer may, for example, only extend to the cancellous region within the ring shaped hole 337.

Reamer 580 is depicted as creating ring shaped hole 337, however variations in the operative end 592 may create cuts and/or openings for other devices and the other embodiments of the hemiarthroplasty device described herein. Reamer 580 prepares a bone surface (e.g. metatarsal head 326) to conform to posts, rings, and cylinders of the implants described herein (e.g. implants 2, 30, 50, 70, 90, 110, 130, 150, 170, 190, 210, 260, 280, 300, 360, 380, 400, 420, 440, 460, 480, 500, 520, 540, 600, 620, 640, 660, 680, and 720).

While reamer 580 is described for bone preparation, other devices may be used to prepare bones for use with the implants described herein (e.g., implants 2, 30, 50, 70, 90, 110, 130, 150, 170, 190, 210, 260, 280, 300, 360, 380, 400, 420, 440, 460, 480, 500, 520, 540, 600, 620, 640, 660, 680, and 720), including, for example, reamers or cutting devices having appropriate shapes and dimensions.

Figure 42:
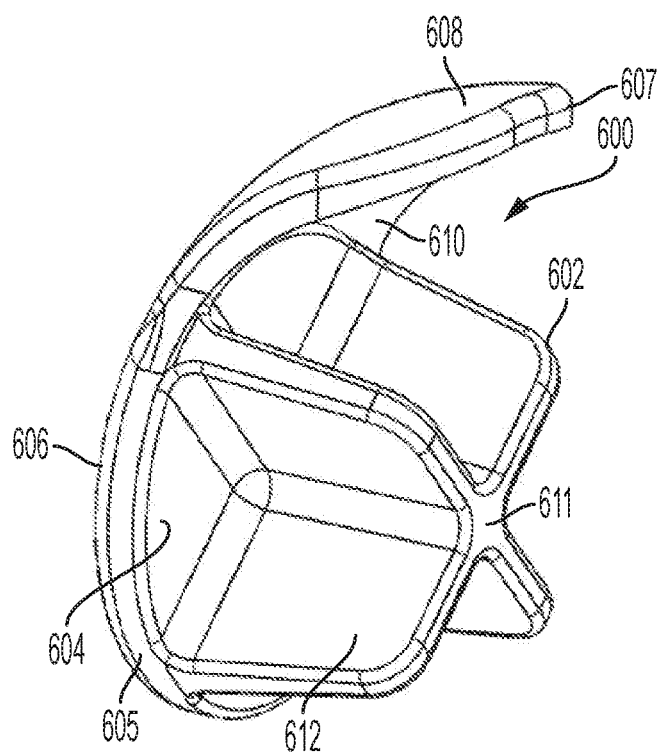
FIG. 42 is a perspective view of a hemiarthroplasty device with endosteal contact ribs, in accordance with an aspect of the present invention.

With reference to FIG. 42 another embodiment is depicted as an endosteal hemiarthroplasty device or an implant 600 having an exterior surface or joint facing surface 606 and a bone facing surface 604 forming a body 605 therebetween. Joint facing surface 606 and bone facing surface 604 are depicted extending dorsally towards an exterior surface 608 and an interior surface 610, respectively, from body 605 forming a dorsal hood 607 therebetween. Body 605 may, for example, have a circular shape, forming an ovular button shape extending towards dorsal hood 607. Dorsal hood 607 may also, for example, curve towards interior surface 610. A cross or "X" shaped extension, ribs 602, may extend out from bone facing surface towards end 611. Ribs 602 extend from the perimeter of body 605, crossing the approximate center of body 605. Implant 600 may be, for example, inserted into a bone for engagement with an endosteum, after creation of a corresponding bone cavity to receive implant 600.

Figure 43:
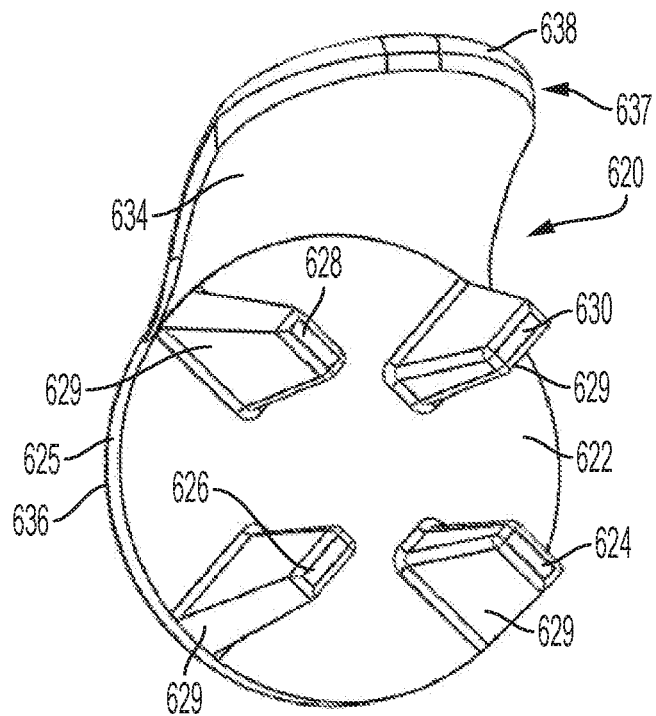
FIG. 43 is a perspective view of a hemiarthroplasty device with endosteal contact posts, in accordance with an aspect of the present invention.

With reference to FIG. 43 another embodiment is depicted as an endosteal hemiarthroplasty device or an implant 620 having an exterior surface or joint facing surface 636 and a bone facing surface 622 forming a body 625 therebetween. Joint facing surface 636 and bone facing surface 622 are depicted extending dorsally towards an exterior surface 638 and an interior surface 634, respectively, from body 625 forming a dorsal hood 637 therebetween. Body 625 may have a circular shape that may, for example, form an ovular button shape extending towards dorsal hood 637. Dorsal hood 637 may also, for example, angled away from joint facing surface 636 in the direction of interior surface 634. A plurality of posts 629 may extend from bone facing surface 622 in a direction away from joint facing surface 636. The plurality of posts 629 may be, for example a first post 630 approximate opposite second post 626 and third post 628 approximately opposite a fourth post 624, with the plurality of posts 629 positioned from the perimeter facing towards the center of body 625. The plurality of posts 629 perimeter facing surface may be angled towards the center of body 625. Implant 620 may be, for example inserted into a bone for engagement with an endosteum, after creation of a corresponding bone cavity to receive implant 620.

Figure 44:
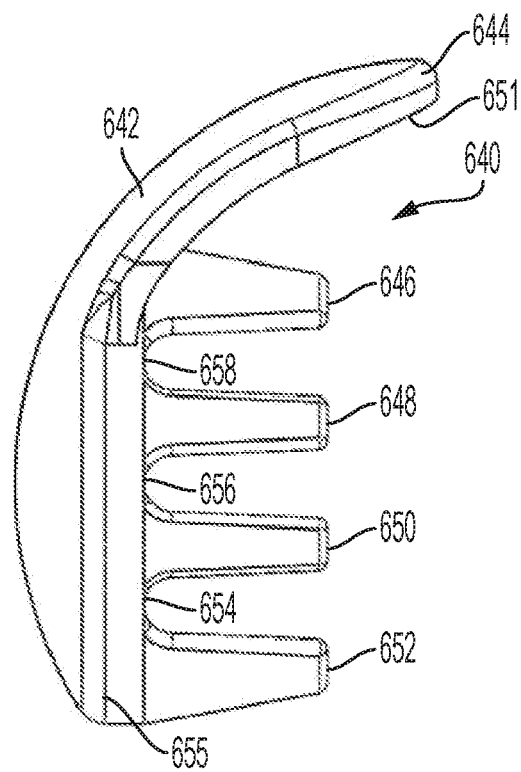
FIG. 44 is a side perspective view of a hemiarthroplasty device with transverse plane engagement ribs, in accordance with an aspect of the present invention.
Figure 45:
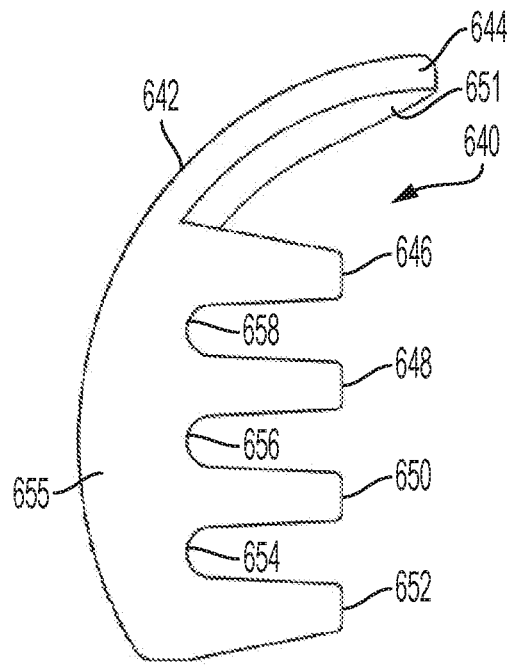
FIG. 45 is a cross-section view of the hemiarthroplasty device of FIG. 44, in accordance with an aspect of the present invention.
Figure 46:
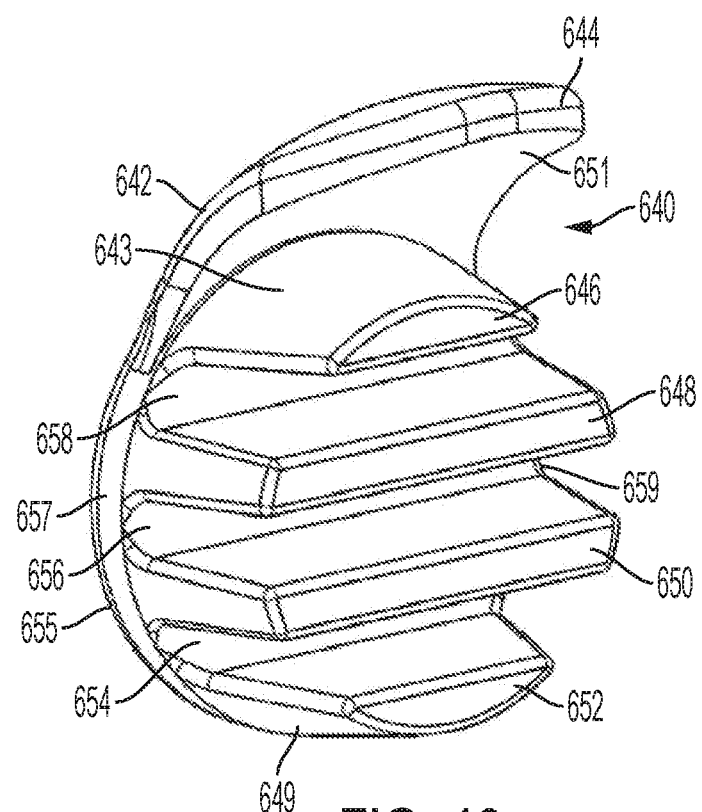
FIG. 46 is a perspective view of the hemiarthroplasty device of FIG. 44, in accordance with an aspect of the present invention.

With reference to FIGS. 44-46, another embodiment is depicted as a ribbed hemiarthroplasty device or an implant 640 having an exterior surface or joint facing surface 642 and a bone facing surface 651 forming a body 655 therebetween. Joint facing surface 642 and bone facing surface 651 are depicted extending dorsally away from joint facing surface 642 from body 655 forming a dorsal hood 644 therebetween. Body 655 may have, for example, a circular shape forming an ovular button shape extending towards dorsal hood 644. Dorsal hood 644 may also, for example, curve towards bone facing surface 651. A plurality of transverse ribs extend out from body 655 from bone facing surface 651. A first rib 646 is positioned at the base of dorsal hood 644. A second rib 648 is below first rib 646. A third rib 650 is below second 648. A fourth rib 652 is below third rib 650, and along the plantar perimeter of body 655. A first trough 658 is between first rib 646 and second rib 648. A second trough 656 is between second rib 648 and third rib 650. A third trough 654 is between third rib 650 and fourth rib 652. The plurality of transverse ribs extend from the first side 657 to the second side 659 of body 655. First rib 656 has a curved dorsal region 643. Fourth rib 652 has a curved plantar region 649.

Figure 47:
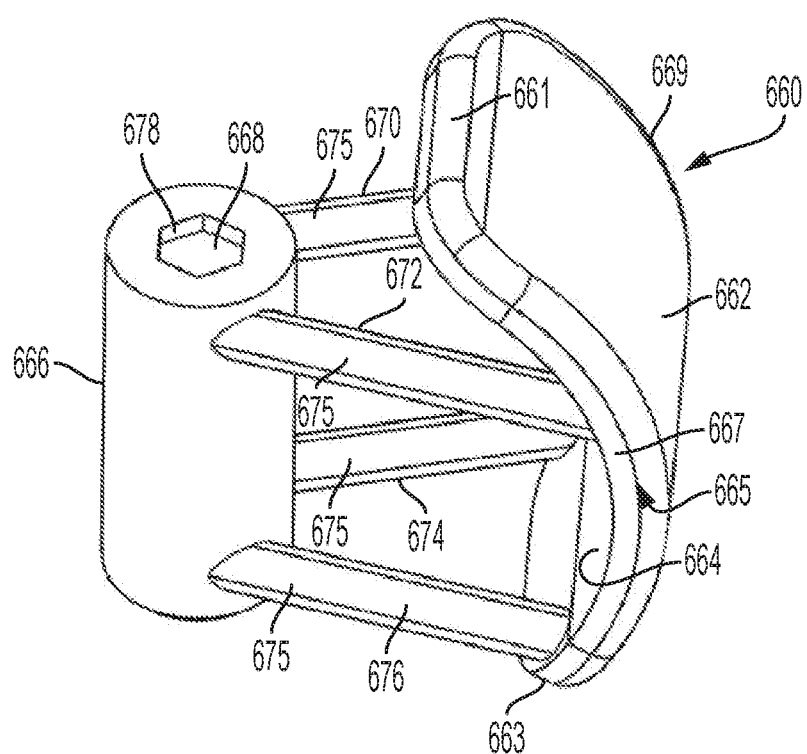
FIG. 47 is a perspective view of a discrete anchoring structure hemiarthroplasty device, in accordance with an aspect of the present invention.

With reference to FIG. 47 another embodiment is depicted as an anchored post hemiarthroplasty device or an implant 660 having an exterior surface or joint facing surface 662 and a bone facing surface 664 forming a body 665 therebetween. Body 665 is depicted as having a rectangular shape and may have, for example rounded edges. Body 665 may, for example, have a first end 661 and a second end 663 curving towards each other, forming a concave bone facing side 664 and a convex joint facing side 662. Body 665 may, for example, have a first side 667 and a second side 669. A plurality of posts 675, are depicted as being canted or angled extending from bone facing surface 664 and connecting with an anchored post 666. Plurality of posts 675 may be, for example, positioned towards the edges of bone facing surface 694. Plurality of posts 675 may, for example, be positioned such that a first post 670 is positioned approximately at second side 199, a second post 672 is positioned approximately at first side 667, a third post 674 is positioned approximately at second end 6633 and second side 669, and a fourth post 676 is positioned approximately at second end 663 and first side 667. Central post 666 is depicted as being cylindrical with a hexagonal opening 678, extending into the interior 668 of central post 666. Central post 666 is configured (e.g. shaped and dimensioned) for receiving, for example, a post, a hexagonal post, or a screw through opening 678.

Figure 48:
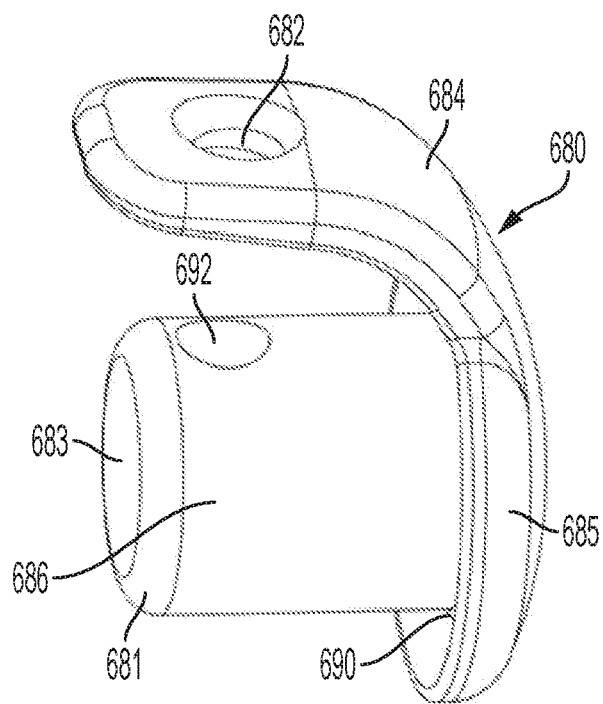
FIG. 48 is perspective view of a canal post hemiarthroplasty device, in accordance with an aspect of the present invention.
Figure 49:
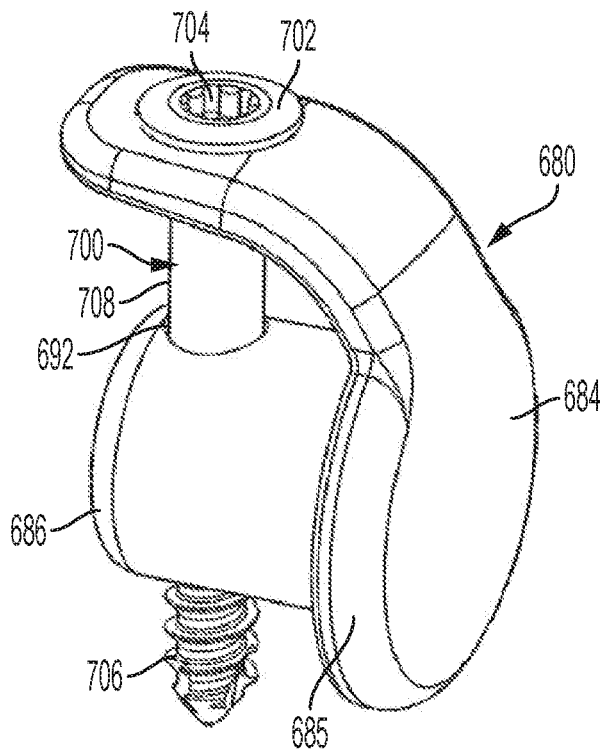
FIG. 49 is a perspective view of the canal post hemiarthroplasty device of FIG. 48 with a screw, in accordance with an aspect of the present invention.

With reference to FIGS. 48 and 49, another embodiment is depicted as a single post hemiarthroplasty device or an implant 680 having an exterior surface or joint facing surface 684 and a bone facing surface 690 forming a body 685 therebetween. Joint facing surface 684 and bone facing surface 690 are depicted extending dorsally from body 685 forming a dorsal hood 684 therebetween. Body 685 may, for example, form a button shape with dorsal hood 684 curving or extending at an angle in the direction of the bone facing surface 690, away from joint facing surface 684. A post 686, having a cylindrical shape, is depicted extending away from bone facing surface 690 towards a tapered region 681 and a free end 683. Dorsal hood 684 is depicted as having a hole 682 above a hole 692 in post 686, with hole 692 extending from the dorsal to plantar end of post 686. Hole 692 is depicted as being towards free end 683. A screw 700 is depicted as inserted through hole 682 and through hole 692. Screw 700 is depicted as having a head 702 with an engagement slot 704 and a shaft 708 extending from head 702 towards an opposite threaded end 706. The sections of body 685 surrounding post 686 are depicted as being concave.

Figure 50:
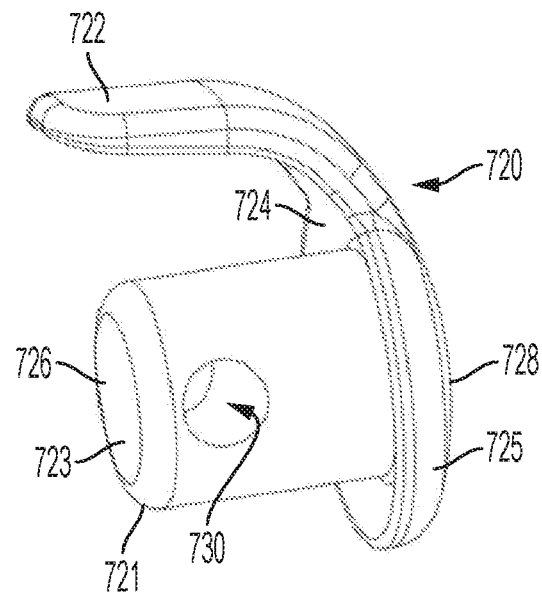
FIG. 50 is a perspective view of a canal post hemiarthroplasty device, in accordance with an aspect of the present invention.
Figure 51:
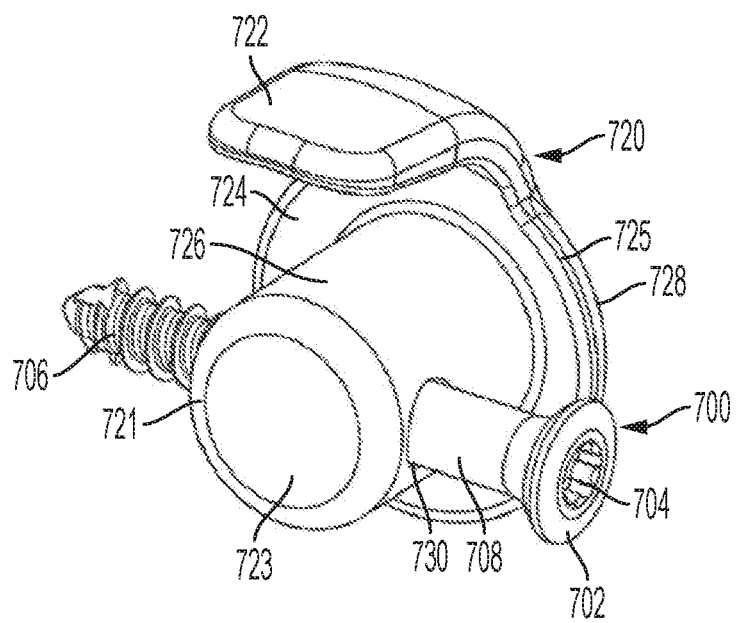
FIG. 51 is a perspective view of the canal post hemiarthroplasty device of FIG. 50 with transverse screw, in accordance with an aspect of the present invention.

With reference to FIGS. 50 and 51, another embodiment is depicted as a single post hemiarthroplasty device or an implant 720 having an exterior surface or joint facing surface 728 and a bone facing surface 724 forming a body 725 therebetween. Joint facing surface 728 and bone facing surface 724 are depicted extending dorsally from body 725 forming a dorsal hood 722 therebetween. Body 725 may, for example, form a button shape with dorsal hood 722 curving or extending at an angle in the direction of the bone facing surface 724, away from joint facing surface 728. A post 726, having a cylindrical shape, is depicted extending away from bone facing surface 724 towards a tapered region 721 and a free end 723. Post 726 is depicted as having a transverse hole 730 extending through post 726 towards free end 723. A screw 700 is depicted as inserted through hole 730. Screw 700 is depicted as having a head 702 with an engagement slot 704 and a shaft 708 extending from head 702 towards an opposite threaded end 706.

In certain embodiments described herein, central posts (e.g. central post 64, central post 82, central post 102. central post 120, and 310) may be used to fill k-wire holes created during bone preparation.

The range of angles of a joint between metatarsal bone 320 and phalange 340 may be from, for example, the bones being colinear to the bones being at 90° to each other. The presence of a dorsal hood or member, as described herein, provides for protection of a dorsal surface of metatarsal bone 320, in particular, the dorsal section of metatarsal head 326 area. A plantar hood 277 may also, for example, be used to protect the plantar region of metatarsal head 326, in particular a region between sesamoid bones of a foot (not shown). Furthermore, the embodiments described in FIGS. 1, 3-6, 10-14, 16, 17, 23, and 42-51 may be, for example, configured (e.g. shaped and dimensioned) such that the dorsal hood is used as a plantar hood for placement between sesamoid bones and to protect the plantar region of metatarsal head 326.

The embodiments described herein provide for posts (e.g. posts 10, 16, 36, 52, 56, 58, 64, 64, 78, 80, 82, 84, 102, 116, 118, 120, 124, 138, 156, 158, 160, 176, 178, 180, 196, 198, 200, 202, 204, 206, 266, 290, 310, 388, 507, 530, and 686) which may be, for example placed into holes extending into the cancellous layer of bone. However, to promote bone preservation, the implant embodiments described herein, in particular the embodiments described in FIGS. 6, 8, 17, 21, 22, 23, 24, and 35-38, use ring elements (e.g. rings 94, 136, 304, 393, 526) for insertion into bone, with the remainder of the bone facing surface providing support along the cortical bone layer of metatarsal bone 320 and phalange 340. The various rings and posts of the implants described in FIGS. 1-39 and 42-51 provide for implant fixation while the remainder of the device provides for load bearing. By using fixation posts or rings, cortical bone removal and preparation is minimized, thus providing for bone preservation. Implants rest on and are supported by the metatarsal head or on a prepared surface within the cortical bone layer of a bone with minimal invasiveness into cancellous bone. The bone facing surfaces of the various embodiments (e.g. the bone facing surfaces described in FIGS. 1-39 and 42-51) may, for example, be in contact with metatarsal head 326 and bone surface 322. By using implants as described herein, subsidence is inhibited, minimized or prevented and bone deterioration is minimized.

With further reference to the implants described herein (e.g. implants 2, 30, 50, 70, 90, 110, 130, 150, 170, 190, 210, 260, 280, 300, 360, 380, 400, 420, 440, 460, 480, 500, 520, 540, 600, 620, 640, 660, 680, and 720), placement on a bone surface (e.g. metatarsal head 326 and/or metatarsal end 344) inhibits bone on bone contact resulting from joint and bone deterioration. Furthermore, implants with dorsal hood elements (e.g. 2, 50, 70, 90, 260, 280, 300, 380, 600, 620, 640, 680, and 720) may, for example, provide protection for a dorsal region of a bone, inhibiting bone on bone for joints in motion. Implants (e.g. implants 170, 190, and 210) with bodies configured (e.g. shapes and dimensioned) for contact with both a dorsal region and a bone surface (e.g. metatarsal head 326 and/or metatarsal end 344) may also, for example provide protection for the dorsal region and bone surface form bone on bone contact.

With reference to FIGS. 1-39 and 42-51, the various implants and devices described above (e.g. implants 2, 30, 50, 70, 90, 110, 130, 150, 170, 190, 210, 260, 280, 300, 360, 380, 400, 420, 440, 460, 480, 500, 520, 540, 600, 620, 640, 660, 680, and 720) may be fabricated from, for example, cobalt chrome and/or a polymer, such as Bionate® or polycarbonate urethane, or other material configured for arthroplasty as described above.

The various implants and devices described above (e.g. implants 2, 30, 50, 70, 90, 110, 130, 150, 170, 190, 210, 260, 280, 300, 360, 380, 400, 420, 440, 460, 480, 500, 520, 540, 600, 620, 640, 660, 680, and 720) described herein may, for example, vary with the with the size and shape of the metatarsal bone 320, the phalange 340, and the level of bone deterioration thereof.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. An implant comprising:
a joint facing surface and a bone facing surface forming a body member therebetween;
an axial end of a central post directly connected to, and extending out from, a first portion of the bone facing surface and configured to be received in a bone recess in a bone created during a preparation of the bone;
a ring member extending out from a second portion of the bone facing surface spaced from the first portion to a free end disposed for insertion into a second bone recess of the bone created during the preparation of the bone, said ring member having a radial outermost surface spaced radially inwardly from a radial outermost surface of said body and a radial innermost surface radially spaced from said central post;
a dorsal member extending from a dorsal end of the body member; and
wherein the dorsal member extends radially and axially from a circumferentialmost portion of the body member, wherein the dorsal member comprises an inner surface and an outer surface.

2. The implant of claim 1, wherein the dorsal member comprises a convex exterior surface and a concave bone facing surface.

3. The implant of claim 2, wherein the ring member comprises a barb for promoting fixation of the bone.

4. The implant of claim 3, wherein the ring member is inset from the perimeter of the body member and the bone facing surface comprises an inset region between the perimeter of the body member and the ring member.

5. The implant of claim 4, wherein the inset region is concave.

6. The implant of claim 1, wherein the post is centered on the bone facing surface of the body member.

7. The implant of claim 6, wherein the ring member is concentric with the post.

8. The implant of claim 7, wherein the post is barbed.

9. The implant of claim 1, wherein the ring member is centered on the body member.

10. The implant of claim 9, wherein the ring member comprises a barb.

11. The implant of claim 10, wherein the dorsal member further comprises a hole extending from the outer surface to the inner surface.

12. The implant of claim 1 further comprising a screw plug for retaining said post.

13. The implant of claim 1 wherein said post extends axially away from said bone facing surface further than said free end of said ring member.

14. The implant of claim 1 wherein said radial innermost surface, said central post and said bone facing surface bound a cavity for receiving a screw plug.

15. An implant comprising:
a joint facing surface and a bone facing surface forming a body member therebetween;
an axial end of a central post directly connected to, and extending out from, a first portion of the bone facing surface and configured to be received in a bone recess in a bone created during a preparation of the bone;
a ring member extending out from a second portion of the bone facing surface spaced from the first portion to a free end disposed for insertion into a second bone recess of the bone created during the preparation of the bone, said ring member having a radial outermost surface spaced radially inwardly from a radial outermost surface of said body and a radial innermost surface radially spaced from said central post;
a dorsal member extending from a dorsal end of the body member;
and
a screw plug for retaining said post.

16. An implant comprising:
a joint facing surface and a bone facing surface forming a body member therebetween;
an axial end of a central post directly connected to, and extending out from, a first portion of the bone facing surface and configured to be received in a bone recess in a bone created during a preparation of the bone;
a ring member extending out from a second portion of the bone facing surface spaced from the first portion to a free end disposed for insertion into a second bone recess of the bone created during the preparation of the bone, said ring member having a radial outermost surface spaced radially inwardly from a radial outermost surface of said body and a radial innermost surface radially spaced from said central post;

a dorsal member extending from a dorsal end of the body member; and wherein said radial innermost surface, said central post and said bone facing surface bound a cavity for receiving a screw plug.

\* \* \* \* \*